US008067372B2

(12) United States Patent
Paris et al.

(10) Patent No.: US 8,067,372 B2
(45) Date of Patent: Nov. 29, 2011

(54) MODULATION OF ANGIOGENESIS BY A-BETA PEPTIDE FRAGMENTS

(75) Inventors: Daniel Paris, Sarasota, FL (US); Michael J. Mullan, Tampa, FL (US)

(73) Assignee: Alzheimer's Institute of America, Inc., Kansas City, KS (US)

( * ) Notice: Subject to any disclaimer, the term of this patent is extended or adjusted under 35 U.S.C. 154(b) by 1194 days.

(21) Appl. No.: 11/598,299

(22) Filed: Nov. 13, 2006

(65) Prior Publication Data

US 2008/0031954 A1  Feb. 7, 2008

Related U.S. Application Data

(60) Provisional application No. 60/735,472, filed on Nov. 10, 2005.

(51) Int. Cl.
*A61K 38/00*  (2006.01)
*A61P 35/00*  (2006.01)
*C07K 14/515*  (2006.01)

(52) U.S. Cl. .................................... 514/13.3

(58) Field of Classification Search ................ None
See application file for complete search history.

(56) References Cited

U.S. PATENT DOCUMENTS

| 3,105,009 | A |   | 9/1963 | Roberts |
|---|---|---|---|---|
| 5,434,050 | A |   | 7/1995 | Maggio et al. |
| 5,981,471 | A |   | 11/1999 | Papathanassiu et al. |
| 6,043,283 | A | * | 3/2000 | Giulian .................... 514/617 |
| 7,589,168 | B2 | * | 9/2009 | Paris et al. ................ 530/300 |
| 2003/0077261 | A1 | * | 4/2003 | Paris et al. ............. 424/93.21 |

FOREIGN PATENT DOCUMENTS

| WO | 94/10569 A1 | 5/1994 |
|---|---|---|
| WO | 94/12627 A1 | 6/1994 |
| WO | 96/28471 A1 | 3/1996 |
| WO | 96/12736 A2 | 5/1996 |
| WO | 97/21728 A1 | 6/1997 |
| WO | 98/11923 A1 | 3/1998 |
| WO | 01/39796 A2 | 6/2001 |
| WO | 01/76558 A1 | 10/2001 |
| WO | 03/014329 A2 | 2/2003 |
| WO | WO03/014329 * | 2/2003 |
| WO | 03/082266 A1 | 10/2003 |
| WO | 2007/059000 A2 | 5/2007 |

OTHER PUBLICATIONS

Wadler et al. Antineoplastic Activity of the Combination of Interferon and Cytotoxic Agents against Experimental and Human Malignancies: A Review. Cancer Research, Jun. 15, 1990, vol. 50, pp. 3473-3486.*
Thorne, et al., "Delivery of Neurotrophic Factors to the Central Nervous System", (2001) Clin. Pharmacokinet., 40 (12): 907-946.
Griffioen, et al.,"Angiogenesis: Potentials for Pharmacologic Intervention in the Treatment of Cancer, Cardiovascular Diseases, and Chronic Inflammation", (2000) Pharmacological Reviews, 52 (2): 237-268.
Vagnucci et al.,"Alzheimer's disease and angiogenisis", (2003) Lancet, 361: 605-607.
Sivakumar, et al., "Modulating Angiogenesis More vs Less", (2004) JAMA, 292(8): 972-977.
Comments (2003), "Alzheimer's disease and angiogenesis", Lancet, 361 (9365) 1298-1300.
Rudinger J. "Characteristics of the amino acids as components of a peptide hormone sequence" (1976), University Park Press, Baltimore, MD., 1-7.
Bowie, et al "Deciphering the Message in Protein Sequences: Tolerance to Amino Acid Substitutions" (1990) Science, 247: 1306-1310.
International Search Report for PCT/US2006/043921 dated Mar. 20, 2008.
Findeis et al., "Modified-Peptide Inhibitors of Amyloid B-Peptide Polymerization" Biochemistry 38(21), 1999, 6791-6800.
Paris, et al., Society for Neuroscience Abstracts 27, 2001, 925.
Paris, et al., "Anti-angiogenic activity of the mutant Dutch AB peptide on human brain microvascular endothelial cells" Molecular Brain Research 136(2), 2005, 212-230.
Supp. EP Search Report for EP 06 83 7407 dated Oct. 26, 2009.
Supp. EP Search Report for EP 02 75 9452 dated Apr. 27, 2006.
International Search Report for PCT/US02/27040 dated Oct. 29, 2003.
International Search Report for PCT/US2009/045079 dated Jan. 22, 2010.
Goldbrunner et al., "Models for Assessment of Angiogenesis in Gliomas," Journal of Neuro-Oncology 50, 2000, pp. 53-62.
Sausville, et al., "Contributions of Human Tumor Xenografts to Anticancer Drug Development," Cancer Res. 66(7), 2006, 3351-3354.
Suggitt, et al., "50 Years of Preclinical Anticancer Drug Screening: Empirical to Target-Driven Approaches," Clinical Cancer Research, vol. 11, 2005, 971-981.
Fidler, Isaiah J., "Regulation of Neoplastic Angiogenesis," Journal of the National Cancer Institute Monographs, vol. 28, 2000, 10-14.
Ngo, et al., "Computational Complexity, Protein Structure Prediction, and the Levinthal Paradox," The Protein Folding Problem and Tertiary Structure Prediction, Merz and Le Grand, eds., 1994, 491-495.
Mendis, D. B. et al. "SPARC/Osteonectin mRNA is induced in Blood Vessels Following Injury to the Adult Rat Cerebral Cortex" Neurochemical Res., 1998, 23(8): 1117-1123. Tarkowski et al., "Increased intrathecal levels of the angiogenic factors VEGF and TGF-beta in Alzheimer's disease and vascular dementia." Neurobiology of Aging. 2002, vol. 23, 237-243.
Paris et al., "Soluble beta-amyloid peptides mediate vasoactivity via activation of a pro-inflammatory pathway." Neurobiology of Aging. 2000, vol. 21, 183-197.
Paris D. et al., "Inhibition of Angiogenesis by AB Peptides" Angiogenesis, 2004, 7:75-85.
Ho L. et al. "The Alternatively Spliced Kunitz Protease Inhibitor Domain Alterns Amyloid B Protein Precursor Processing and Amyloid B Protein Production in Cultured Cells", J. Biol. Chem., 1996; 271 (48): 30929-30394.
Ramakrishnan et al., 2001, Targeting tumor vasculature using VEGF-toxin Conjugates. Methods Mol Biol 166: 219-234.
De Sauvage, F. et al. "Novel mRNA of the A4 Amyloid Precursor Gene Coding for a Possibly Secreted Protein" Science, 1989, 245(4918): 651-653.

(Continued)

*Primary Examiner* — Marcela M Cordero Garcia
(74) *Attorney, Agent, or Firm* — Bryan Cave LLP

(57) ABSTRACT

Provided are Aβ peptide fragments that are useful in inhibiting angiogenesis. Also provided are methods for the treatment of pathological or unwanted angiogenesis and conditions and diseases associated therewith by administering an effective amount of an Aβ fragment. In a particular embodiment, the peptide fragment includes the sequence HHQKLVFF.

20 Claims, 16 Drawing Sheets

OTHER PUBLICATIONS

Ellis, R. J. et al. "Cerebral amyloid angiopathy in the brains of patents with Alzheimer's disease: The CERAD experience, part XV" Neurology, 1996, 46: 1592-1596.

Folkman, J. "How is Blood Vessel Growth Regulated in Normal and Neoplastic Tissue?—G.H.A. Clowes Memorial Award Lecture" Cancer Research, Feb. 1986, 46:467-473.

Folkman, J. "What is the Evidence That Tumors Are Angiogenesis Dependent?" Journal of the National Cancer Institute, Jan. 3, 1990, 82(1): 4-6.

Hashimoto, T. et al. "Abnormal Balance in the Angiopoietin-Tie2 System in Human Brain Arteriovenous Malformations" Circ. Res. 2001, 89:111-113.

Hashimura, T. et al., "Morphological Changes of Blood Vessels in the Brain with Alzheimer's Disease" Jpn. J. Psychiatry Neurol., 1991, 45 (3): 661-665.

Johnson, K. and M. S. Albert "Perfusion abnormalities in prodromal AD" Neurobiology of Aging, 2000, 21:289-292.

Kalaria, R.N. "The Blood-Brain Barrier and Cerebrovascular Pathology in Alzheimer's Disease" Ann. N. Y. Acad. Sci., 1999, 893:113-125.

Kimura, T. et al. "Observations of Microvessels in the Brain with Alzheimer's Disease by the Scanning Electron Microscopy" Jpn. J. Psychiatry Neurol., 1991, 45(3): 671-676.

Kruger, E. A. et al. "Endostatin Inhibits Microvessel Formation in the ex Vivo Rat Aortic Ring Angiogenesis Assay" Biochem. Biophys. Res. Commun., 2000, 268:183-191.

Nagata, K. et al. "Vascular and metabolic reserve in Alzheimer's disease" Neurobiology of Aging, 2000, 21:301-307.

Naidu, A. et al. "B-Amyloid Peptide produced in Vitro Is Degraded by Proteinases Related by Cultured Cells" J. Biol. Chem., 1995, 270(3): 1369-1374.

Nicosia, R. F. et al. "Large-vessel endothelium switches to a microvascular phenotype during angiogenesis in collagen gel culture of rat aorta" Atherosclerosis, 1992, 95: 191-199.

Nicosia, R. F. et al., "Endogenous Regulation of Angiogenesis in the Rat Aorta Model" Amer. J. Path., Nov. 1997, 151(5): 1379-1386.

Ponte, P. et al., "A new A4 amyloid mRNA contains a domain homologous to serine proteinase inhibitors" Nature, Feb. 1988 331:525-527.

Sisodia, S. et al. "Role of the B-amyloid Protein in Alzheimer's disease" FASEB. J., 1995, 9:366-370.

Slevin, M. et al., "Serial Measurement of Vascular Endothelial Growth Factor and Transforming Growth Factor-B1 in Serum of Patients With Acute Ischemic Stroke" Stroke, 2000, 31: 1863-1870.

Weidner, N. et al., "Tumor Angiogenesis and Metastas—Correlation in Invasion Breast Carcinoma" The New England Journal of Medicine, 1991, 324(1):1-8.

Yoshikai, S. et al. "Genomic organization of the human amyloid beta-protein precursor gene" Gene, 1990, 87:257-263.

Flood J. F. et al., "Amnestic effects in mice of four synthetic peptides homologous to amyloid B protein from patients with Alzheimer disease" Proceedings of the National Academy of Sciences, USA (1991)88 (8): 3363-3366.

Tjernberg, L.O. et al. "Arrest of B-Amyloid Fibril Formation by a Pentapeptide Ligand" Journal of Biological Chemistry (1996) 271 (15): 8545-8548.

Paivio, A. et al., "Unique Physicochemical Profile of B-Amyloid Peptide Variant AB1-40E22G Protofibrils: Conceivable Neuropathogen in Arctic Mutant Carriers" Journal of Molecular Biology (2004) 339 (1): 145-159.

Deonarain, "Ligand-targeted receptor-mediated vectors for gene delivery", (1998) Exp. Opin. Ther. Pat., 8(1): 53-69.

Gorecki, "Prospects and problems of gene therapy: an update", (2001) Exp. Opin. Emerging Drugs, 6 (2): 187-198.

Verma, et al., "Gene therapy—promises, problems and prospects", (1997) Nature, 389: 239-242.

Eck, et al., "Gene-Based Therapy", (1996) Goodman & Gilman's The Pharmacological Basis of Therapeutics, 9th Ed., Mcgraw-Hill, New York, NY., 77-101.

* cited by examiner

*a*) VEGF control (200ng); *b*) Aβ12-28 (0.5μg); *c*) Aβ12-28 (2.5μg); *d*) Aβ12-28 (5.0μg)

SEQUENCE LISTING

<160> NUMBER OF SEQ ID NOS: 11

<210> SEQ ID NO 1
<211> LENGTH: 43
<212> TYPE: PRT
<213> ORGANISM: Homo sapiens
<220> FEATURE:
<221> NAME/KEY: PEPTIDE
<222> LOCATION: (1)..(43)
<223> OTHER INFORMATION: A-beta 1-43 peptide

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
        35                  40

<210> SEQ ID NO 2

```
<211> LENGTH: 42
<212> TYPE: PRT
<213> ORGANISM: Homo sapiens
<220> FEATURE:
<221> NAME/KEY: PEPTIDE
<222> LOCATION: (1)..(42)
<223> OTHER INFORMATION: A-beta 1-42 peptide

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 3
<211> LENGTH: 40
<212> TYPE: PRT
<213> ORGANISM: Homo sapiens
<220> FEATURE:
<221> NAME/KEY: PEPTIDE
<222> LOCATION: (1)..(40)
<223> OTHER INFORMATION: A-beta 1-40 peptide

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 4
<211> LENGTH: 40
<212> TYPE: PRT
<213> ORGANISM: Artificial Sequence
<220> FEATURE:
<223> OTHER INFORMATION: scrambled A-beta 1-40 peptide

<400> SEQUENCE: 4

Val Ile Gly Lys Tyr His Gly Met Ser Asn Leu Val Gly Arg Ser Phe
1               5                   10                  15

Glu Val His Gln Gly Lys Gly Ala Glu Val Asp Ala His Gly Leu Phe
            20                  25                  30

Asp Ile Glu Ala Phe Val Asp Val
        35                  40

<210> SEQ ID NO 5
<211> LENGTH: 770
<212> TYPE: PRT
<213> ORGANISM: Homo sapiens
<220> FEATURE:
<221> NAME/KEY: MISC_FEATURE
<222> LOCATION: (1)..(770)
<223> OTHER INFORMATION: Amyloid precursor protein

<400> SEQUENCE: 5

Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30
```

```
Gln Ile Ala Met Phe Cys Gly Arg Leu Asn Met His Met Asn Val Gln
    35                  40                  45
Asn Gly Lys Trp Asp Ser Asp Pro Ser Gly Thr Lys Thr Cys Ile Asp
50                  55                  60
Thr Lys Glu Gly Ile Leu Gln Tyr Cys Gln Glu Val Tyr Pro Glu Leu
65                      70                  75                  80
Gln Ile Thr Asn Val Val Glu Ala Asn Gln Pro Val Thr Ile Gln Asn
            85                  90                  95
Trp Cys Lys Arg Gly Arg Lys Gln Cys Lys Thr His Pro His Phe Val
            100                 105                 110
Ile Pro Tyr Arg Cys Leu Val Gly Glu Phe Val Ser Asp Ala Leu Leu
        115                 120                 125
Val Pro Asp Lys Cys Lys Phe Leu His Gln Glu Arg Met Asp Val Cys
    130                 135                 140
Glu Thr His Leu His Trp His Thr Val Ala Lys Glu Thr Cys Ser Glu
145                 150                 155                 160
Lys Ser Thr Asn Leu His Asp Tyr Gly Met Leu Leu Pro Cys Gly Ile
                165                 170                 175
Asp Lys Phe Arg Gly Val Glu Phe Val Cys Cys Pro Leu Ala Glu Glu
            180                 185                 190
Ser Asp Asn Val Asp Ser Ala Asp Ala Glu Glu Asp Asp Ser Asp Val
        195                 200                 205
Trp Trp Gly Gly Ala Asp Thr Asp Tyr Ala Asp Gly Ser Glu Asp Lys
    210                 215                 220
Val Val Glu Val Ala Glu Glu Glu Val Ala Glu Val Glu Glu Glu
225                 230                 235                 240
Glu Ala Asp Asp Asp Glu Asp Asp Glu Asp Gly Asp Glu Val Glu Glu
                245                 250                 255
Glu Ala Glu Glu Pro Tyr Glu Glu Ala Thr Glu Arg Thr Thr Ser Ile
            260                 265                 270
Ala Thr Thr Thr Thr Thr Thr Glu Ser Val Glu Glu Val Val Arg
    275                 280                 285
Glu Val Cys Ser Glu Gln Ala Glu Thr Gly Pro Cys Arg Ala Met Ile
    290                 295                 300
Ser Arg Trp Tyr Phe Asp Val Thr Glu Gly Lys Cys Ala Pro Phe Phe
305                 310                 315                 320
Tyr Gly Gly Cys Gly Gly Asn Arg Asn Asn Phe Asp Thr Glu Glu Tyr
                325                 330                 335
Cys Met Ala Val Cys Gly Ser Ala Met Ser Gln Ser Leu Leu Lys Thr
            340                 345                 350
Thr Gln Glu Pro Leu Ala Arg Asp Pro Val Lys Leu Pro Thr Thr Ala
        355                 360                 365
Ala Ser Thr Pro Asp Ala Val Asp Lys Tyr Leu Glu Thr Pro Gly Asp
    370                 375                 380
Glu Asn Glu His Ala His Phe Gln Lys Ala Lys Glu Arg Leu Glu Ala
385                 390                 395                 400
Lys His Arg Glu Arg Met Ser Gln Val Met Arg Glu Trp Glu Glu Ala
                405                 410                 415
Glu Arg Gln Ala Lys Asn Leu Pro Lys Ala Asp Lys Lys Ala Val Ile
            420                 425                 430
```

| | | | | | | | | | | | | | | |
|---|---|---|---|---|---|---|---|---|---|---|---|---|---|---|
| Gln | His | Phe | Gln | Glu | Lys | Val | Glu | Ser | Leu | Glu | Gln | Glu | Ala | Ala | Asn |
| | | 435 | | | | 440 | | | | | 445 | | | | |
| Glu | Arg | Gln | Gln | Leu | Val | Glu | Thr | His | Met | Ala | Arg | Val | Glu | Ala | Met |
| 450 | | | | | 455 | | | | | 460 | | | | | |
| Leu | Asn | Asp | Arg | Arg | Arg | Leu | Ala | Leu | Glu | Asn | Tyr | Ile | Thr | Ala | Leu |
| 465 | | | | 470 | | | | | 475 | | | | | | 480 |
| Gln | Ala | Val | Pro | Pro | Arg | Pro | Arg | His | Val | Phe | Asn | Met | Leu | Lys | Lys |
| | | | | 485 | | | | | 490 | | | | | 495 | |
| Tyr | Val | Arg | Ala | Glu | Gln | Lys | Asp | Arg | Gln | His | Thr | Leu | Lys | His | Phe |
| | | | | 500 | | | | 505 | | | | | 510 | | |
| Glu | His | Val | Arg | Met | Val | Asp | Pro | Lys | Lys | Ala | Ala | Gln | Ile | Arg | Ser |
| | | 515 | | | | | 520 | | | | | 525 | | | |
| Gln | Val | Met | Thr | His | Leu | Arg | Val | Ile | Tyr | Glu | Arg | Met | Asn | Gln | Ser |
| 530 | | | | | 535 | | | | | 540 | | | | | |
| Leu | Ser | Leu | Leu | Tyr | Asn | Val | Pro | Ala | Val | Ala | Glu | Glu | Ile | Gln | Asp |
| 545 | | | | | 550 | | | | | 555 | | | | | 560 |
| Glu | Val | Asp | Glu | Leu | Leu | Gln | Lys | Glu | Gln | Asn | Tyr | Ser | Asp | Asp | Val |
| | | | | 565 | | | | | 570 | | | | | 575 | |
| Leu | Ala | Asn | Met | Ile | Ser | Glu | Pro | Arg | Ile | Ser | Tyr | Gly | Asn | Asp | Ala |
| | | | 580 | | | | | 585 | | | | | 590 | | |
| Leu | Met | Pro | Ser | Leu | Thr | Glu | Thr | Lys | Thr | Thr | Val | Glu | Leu | Leu | Pro |
| | | 595 | | | | | 600 | | | | | 605 | | | |
| Val | Asn | Gly | Glu | Phe | Ser | Leu | Asp | Asp | Leu | Gln | Pro | Trp | His | Ser | Phe |
| 610 | | | | | 615 | | | | | 620 | | | | | |
| Gly | Ala | Asp | Ser | Val | Pro | Ala | Asn | Thr | Glu | Asn | Glu | Val | Glu | Pro | Val |
| 625 | | | | | 630 | | | | | 635 | | | | | 640 |
| Asp | Ala | Arg | Pro | Ala | Ala | Asp | Arg | Gly | Leu | Thr | Thr | Arg | Pro | Gly | Ser |
| | | | | 645 | | | | | 650 | | | | | 655 | |
| Gly | Leu | Thr | Asn | Ile | Lys | Thr | Glu | Glu | Ile | Ser | Glu | Val | Lys | Met | Asp |
| | | | 660 | | | | | 665 | | | | | 670 | | |
| Ala | Glu | Phe | Arg | His | Asp | Ser | Gly | Tyr | Glu | Val | His | His | Gln | Lys | Leu |
| | | | 675 | | | | | 680 | | | | | 685 | | |
| Val | Phe | Phe | Ala | Glu | Asp | Val | Gly | Ser | Asn | Lys | Gly | Ala | Ile | Ile | Gly |
| | | 690 | | | | | 695 | | | | | 700 | | | |
| Leu | Met | Val | Gly | Gly | Val | Val | Ile | Ala | Thr | Val | Ile | Val | Ile | Thr | Leu |
| 705 | | | | | 710 | | | | | 715 | | | | | 720 |
| Val | Met | Leu | Lys | Lys | Lys | Gln | Tyr | Thr | Ser | Ile | His | His | Gly | Val | Val |
| | | | | 725 | | | | | 730 | | | | | 735 | |
| Glu | Val | Asp | Ala | Ala | Val | Thr | Pro | Glu | Glu | Arg | His | Leu | Ser | Lys | Met |
| | | | 740 | | | | | 745 | | | | | 750 | | |
| Gln | Gln | Asn | Gly | Tyr | Glu | Asn | Pro | Thr | Tyr | Lys | Phe | Phe | Glu | Gln | Met |
| | | | 755 | | | | | 760 | | | | | 765 | | |
| Gln | Asn | | | | | | | | | | | | | | |
| | 770 | | | | | | | | | | | | | | |

<210> SEQ ID NO 6
<211> LENGTH: 3579
<212> TYPE: DNA
<213> ORGANISM: Homo sapiens
<220> FEATURE:
<221> NAME/KEY: misc_feature
<222> LOCATION: (1)..(3579)
<223> OTHER INFORMATION: nucleotide encoding Amyloid precursor protein Figure 10, continued.

-continued

<400> SEQUENCE: 6

```
agtttcctcg gcagcggtag gcgagagcac gcggaggagc gtgcgcgggg gccccgggag    60
acggcggcgg tggcggcgcg ggcagagcaa ggacgcggcg gatcccactc gcacagcagc   120
gcactcggtg ccccgcgcag ggtcgcgatg ctgcccggtt tggcactgct cctgctggcc   180
gcctggacgg ctcgggcgct ggaggtaccc actgatggta atgctggcct gctggctgaa   240
ccccagattg ccatgttctg tggcagactg aacatgcaca tgaatgtcca gaatgggaag   300
tgggattcag atccatcagg gaccaaaacc tgcattgata ccaaggaagg catcctgcag   360
tattgccaag aagtctaccc tgaactgcag atcaccaatg tggtagaagc caaccaacca   420
gtgaccatcc agaactggtg caagcggggc cgcaagcagt gcaagaccca tccccacttt   480
gtgattccct accgctgctt agttggtgag tttgtaagtg atgccottct cgttcctgac   540
aagtgcaaat tcttacacca ggagaggatg gatgtttgcg aaactcatct tcactggcac   600
accgtcgcca aagagacatg cagtgagaag agtaccaact tgcatgacta cggcatgttg   660
ctgccctgcg gaattgacaa gttccgaggg gtagagtttg tgtgttgccc actggctgaa   720
gaaagtgaca atgtggattc tgctgatgcg gaggaggatg actcggatgt ctggtggggc   780
ggagcagaca cagactatgc agatgggagt gaagacaaag tagtagaagt agcagaggag   840
gaagaagtgg ctgaggtgga agaagaagaa gccgatgatg acgaggacga tgaggatggt   900
gatgaggtag aggaagaggc tgaggaaccc tacgaagaag ccacagagag aaccaccagc   960
attgccacca ccaccaccac caccacagag tctgtggaag aggtggttcg agaggtgtgc  1020
tctgaacaag ccgagacggg gccgtgccga gcaatgatct cccgctggta ctttgatgtg  1080
actgaaggga agtgtgcccc attcttttac ggcggatgtg gcggcaaccg gaacaactt   1140
gacacagaag agtactgcat ggccgtgtgt ggcagcgcca tgtcccaaag tttactcaag  1200
actaccagg aacctcttgc ccgagatcct gttaaacttc ctacaacagc agccagtacc  1260
cctgatgccg ttgacaagta tctcgagaca cctggggatg agaatgaaca tgcccatttc  1320
cagaaagcca aagagaggct tgaggccaag caccgagaga gaatgtccca ggtcatgaga  1380
gaatgggaag aggcagaacg tcaagcaaag aacttgccta aagctgataa gaaggcagtt  1440
atccagcatt tccaggagaa agtggaatct ttggaacagg aagcagccaa cgagagacag  1500
cagctggtgg agacacacat ggccagagtg gaagccatgc tcaatgaccg ccgccgcctg  1560
gccctggaga actacatcac cgctctgcag gctgttcctc ctcggcctcg tcacgtgttc  1620
aatatgctaa agaagtatgt ccgcgcagaa cagaaggaca gacagcacac cctaaagcat  1680
ttcgagcatg tgcgcatggt ggatcccaag aaagccgctc agatccggtc ccaggttatg  1740
acacacctcc gtgtgattta tgagcgcatg aatcagtctc tctccctgct ctacaacgtg  1800
cctgcagtgg ccgaggagat tcaggatgaa gttgatgagc tgcttcagaa agagcaaaac  1860
tattcagatg acgtcttggc caacatgatt agtgaaccaa ggatcagtta cggaaacgat  1920
gctctcatgc catctttgac cgaaacgaaa accaccgtgg agctccttcc cgtgaatgga  1980
gagttcagcc tggacgatct ccagccgtgg cattcttttg gggctgactc tgtgccagcc  2040
aacacagaaa acgaagttga gcctgttgat gcccgccctg ctgccgaccg aggactgacc  2100
actcgaccag gttctgggtt gacaaatatc aagacggagg agatctctga agtgaagatg  2160
gatgcagaat tccgacatga ctcaggatat gaagttcatc atcaaaaatt ggtgttcttt  2220
```

```
gcagaagatg tgggttcaaa caaaggtgca atcattggac tcatggtggg cggtgttgtc    2280
atagcgacag tgatcgtcat caccttggtg atgctgaaga agaaacagta cacatccatt    2340
catcatggtg tggtggaggt tgacgccgct gtcaccccag aggagcgcca cctgtccaag    2400
atgcagcaga acggctacga aaatccaacc tacaagttct ttgagcagat gcagaactag    2460
acccccgcca cagcagcctc tgaagttgga cagcaaaacc attgcttcac taccccatcgg   2520
tgtccattta tagaataatg tgggaagaaa caaacccgtt ttatgattta ctcattatcg    2580
cctttttgaca gctgtgctgt aacacaagta gatgcctgaa cttgaattaa tccacacatc   2640
agtaatgtat tctatctctc tttacatttt ggtctctata ctacattatt aatgggtttt    2700
gtgtactgta aagaatttag ctgtatcaaa ctagtgcatg aatagattct ctcctgatta    2760
tttatcacat agccccttag ccagttgtat attattcttg tggtttgtga cccaattaag    2820
tcctacttta catatgcttt aagaatcgat gggggatgct tcatgtgaac gtgggagttc    2880
agctgcttct cttgcctaag tattcctttc ctgatcacta tgcattttaa agttaaacat    2940
ttttaagtat ttcagatgct ttagagagat tttttttcca tgactgcatt ttactgtaca    3000
gattgctgct tctgctatat ttgtgatata ggaattaaga ggatacacac gtttgtttct    3060
tcgtgcctgt tttatgtgca cacattaggc attgagactt caagcttttc tttttttgtc    3120
cacgtatctt tgggtctttg ataaagaaaa gaatccctgt tcattgtaag cacttttacg    3180
gggcgggtgg ggagggtgc tctgctggtc ttcaattacc aagaattctc caaaacaatt    3240
ttctgcagga tgattgtaca gaatcattgc ttatgacatg atcgctttct acactgtatt    3300
acataaataa attaaataaa ataacccgg gcaagacttt tctttgaagg atgactacag     3360
acattaaata atcgaagtaa ttttgggtgg ggagaagagg cagattcaat tttcttttaac  3420
cagtctgaag tttcatttat gatacaaaag aagatgaaaa tggaagtggc aatataagyg    3480
gatgagqaag gcatgcctgg acaaacccctt cttttaagat gtgtcttcaa tttgtataaa   3540
atggtgtttt catgtaaaata aatacattct tggaggagc                         3579
```

<210> SEQ ID NO 7
<211> LENGTH: 42
<212> TYPE: PRT
<213> ORGANISM: Artificial Sequence
<220> FEATURE:
<223> OTHER INFORMATION: 21G-A-beta 1-42 (Flemish) mutant

<400> SEQUENCE: 7

Asp Ala Glu Phe Arg His Asp Ser Gly Tyr Glu Val His His Gln Lys
1               5                   10                  15

Leu Val Phe Phe Gly Glu Asp Val Gly Ser Asn Lys Gly Ala Ile Ile
            20                  25                  30

Gly Leu Met Val Gly Gly Val Val Ile Ala
        35                  40

<210> SEQ ID NO 8
<211> LENGTH: 42
<212> TYPE: PRT
<213> ORGANISM: Artificial Sequence
<220> FEATURE:
<223> OTHER INFORMATION: 22Q-A-beta 1-42 (Dutch) mutant

<400> SEQUENCE: 8

Asp Ala Glu Phe Arg His Asp Ser Gly Tyr Glu Val His His Gln Lys

```
              1               5                  10                 15
Leu Val Phe Phe Ala Gln Asp Val Gly Ser Asn Lys Gly Ala Ile Ile
                        20                  25                 30

Gly Leu Met Val Gly Gly Val Val Ile Ala
            35                  40

<210> SEQ ID NO 9
<211> LENGTH: 42
<212> TYPE: PRT
<213> ORGANISM: Artificial Sequence
<220> FEATURE:
<223> OTHER INFORMATION: 22K-A-beta 1-42 (Italian) mutant

<400> SEQUENCE: 9

Asp Ala Glu Phe Arg His Asp Ser Gly Tyr Glu Val His His Gln Lys
  1               5                  10                 15

Leu Val Phe Phe Ala Lys Asp Val Gly Ser Asn Lys Gly Ala Ile Ile
                        20                  25                 30

Gly Leu Met Val Gly Gly Val Val Ile Ala
            35                  40

<210> SEQ ID NO 10
<211> LENGTH: 42
<212> TYPE: PRT
<213> ORGANISM: Artificial Sequence
<220> FEATURE:
<223> OTHER INFORMATION: 22G-A-beta 1-42 (Arctic) mutant

<400> SEQUENCE: 10

Asp Ala Glu Phe Arg His Asp Ser Gly Tyr Glu Val His His Gln Lys
  1               5                  10                 15

Leu Val Phe Phe Ala Gly Asp Val Gly Ser Asn Lys Gly Ala Ile Ile
                        20                  25                 30

Gly Leu Met Val Gly Gly Val Val Ile Ala
            35                  40

<210> SEQ ID NO 11
<211> LENGTH: 42
<212> TYPE: PRT
<213> ORGANISM: Artificial Sequence
<220> FEATURE:
<223> OTHER INFORMATION: 23N-A-beta 1-42 (Iowa) mutant

<400> SEQUENCE: 11

Asp Ala Glu Phe Arg His Asp Ser Gly Tyr Glu Val His His Gln Lys
  1               5                  10                 15

Leu Val Phe Phe Ala Glu Asn Val Gly Ser Asn Lys Gly Ala Ile Ile
                        20                  25                 30

Gly Leu Met Val Gly Gly Val Val Ile Ala
            35                  40
```

MODULATION OF ANGIOGENESIS BY A-BETA PEPTIDE FRAGMENTS

CROSS REFERENCE TO RELATED APPLICATIONS

This application claims the benefit of priority to U.S. Provisional Application No. 60/735,472 filed Nov. 10, 2005, the disclosure of which is incorporated herein.

FIELD OF THE INVENTION

The present invention is related to compositions and methods for treating diseases and pathological conditions or processes mediated by pathological angiogenesis by administering biologically active fragments of full length Aβ peptides to a patient suffering from such diseases, conditions, or processes.

DESCRIPTION OF RELATED ART

Alzheimer's disease (AD) is the major cause of dementia in the elderly in Western countries, and is characterized by the progressive accumulation of intracellular neurofibrillary tangles, extracellular parenchymal senile plaques, and cerebrovascular deposits (Sissodia, et al. F.A.S.E.B. J. 9:366-370 (1995)). The principal component of senile plaques and cerebrovascular deposits is the β-amyloid peptide, the aggregated form of which consists of the 39-43 amino acid residue Aβ peptides that are proteolytically derived from the amyloid precursor protein (APP) (Naidu, et al. 1995 J. Biol. Chem. 270:1369-1374; Gorevic, et al. 1986 J. Neuropathol. Exp. Neurol. 45, 647-64; Selkoe, et al. 1986 J. Neurochem. 46, 1820-34). The primary protein component of senile plaques is beta/A4 amyloid, a 42-43 amino acid peptide.

Vascular pathology is the norm in advanced cases of AD, with cerebral amyloid angiopathy (CAA) being one of the most common abnormalities detected at autopsy (Ellis, et al. Neurology 46:1592-1596 (1996)). Certain vascular lesions, such as microvascular degeneration affecting the cerebral endothelium and periventricular white matter lesions, are evident in most AD cases (Ellis, et al. Neurology 46:1592-1596 (1996); Kalaria, Ann. N.Y. Acad. Sci. 893:113-125 (1999)). Furthermore, morphological alterations have been observed in AD brain microvessels and capillaries; in particular, terminal arterioles frequently have focal constriction and smooth muscle cells with an irregular shape and arrangement (Hashimura et al. Jpn. J. Psychiatry Neurol. 45:661-665 (1991)). Capillaries in AD brain typically show an abnormal abluminal surface with irregular constriction and dilatation along their paths (Kimura et al. Jpn. J. Psychiatry Neurol. 45:671-676 (1991)). Functional imaging techniques including positron emission tomography (PET) and single photon emission computerized tomography (SPECT) have revealed the existence of hypoperfusion in individuals prior to the time that they meet clinical criteria for AD suggesting that vascular abnormalities occur early during the disease process (Nagata et al. Neurobiology of Aging 21:301-307 (2000); Johnson et al. Neurobiology of Aging 21:289-292 (2000)). In other disorders involving cerebrovascular damage (such as traumatic brain injury, stroke and brain arteriovenous malformation), angiogenesis is a prominent response (Mendis et al. Neurochem. Res. 23:1117-23 (1998); Slevin et al. Stroke 31:1863-70 (2000); Hashimoto et al. Circ. Res. 89:111-3 (2001)). Given the plethora of reports on cerebrovascular damage in AD brain, the induction of an angiogenic reparative response would be expected, although there has been very little work in this area.

Several assays have been developed to study the specific steps involved in the angiogenic process (adhesion, migration, growth, invasion and differentiation). Knowledge of the effects of Aβ on angiogenesis would be of value in understanding its role in the micro-cerebrovascular abnormalities observed in AD. In the AD brain, Aβ peptides are known to form fibrillar deposits around blood vessels, leading to cerebral amyloid angiopathy (CAA) (Pardridge, et al. 1987 J. Neurochem. 49, 1394-401; Jellinger K. A., Attems J. 2005 J. Neurol. Sci. 229-230, 37-41). The increased levels of soluble and deposited Aβ in the AD brain can induce vascular damage, inflammation/gliosis, and reduced cerebral blood flow (Paris, et al. 2000 Ann. N.Y. Acad. Sci. 903, 97-109; Johnson, et al. 2005 Radiology. 234, 851-9). Numerous studies have shown that vascular functional impairments and reduced blood flow are characteristic features of the AD brain (Nicoll, et al. 2004 Neurobiol. Aging. 25, 589-97 and 603-4; Paris, et al. 2004 Brain Res. 999, 53-61; Beckmann, et al. 2003 J. Neurosci. 23, 8453-9; Farkasm, et al. 2001 "Cerebral microvascular pathology in aging and Alzheimer's disease" Prog. Neurobiol. 64, 575-611). Recently, it has been shown that angiogenesis is impaired in AD, and that this is associated with alterations in genes involved in vascular differentiation (Wu, et al. 2005 Nat. Med. 11, 959-65). A reduced brain capillary density is known in transgenic mouse models of AD (Paris, et al. 2004 Neurosci. Lett. 360, 80-5; Lee, et al. 2005 Brain Res. Bull. 65, 317-22). An impaired formation of capillary like structures on reconstituted basement membrane by endothelial cells and arterial explants harvested from the brains of TgAPPsw mice, suggesting abnormal alterations in the angiogenic response in TgAPPsw mice was recently demonstrated. (Paris, et al. 2004 Neurosci. Lett. 360, 80-5).

U.S. Patent Publication No. 2003/0077261 to Paris et al. discloses that Aβ peptides can be used as anti-angiogenic agents, and discloses the sequences of A-Beta peptides and APP as well as the nucleic acids encoding them, which are shown in the attached Sequence Listing.

Angiogenesis is inhibited by Aβ peptides in multiple different in-vitro and in-vivo assays (Paris, et al. 2004 Angiogenesis. 7, 75-85). In-vitro, $A\beta_{1-40}$ and $A\beta_{1-42}$ can dose dependently inhibit capillary tube formation by human brain microvascular endothelial cells when plated on Matrigel, and can promote capillary degeneration at high doses. Mutants of the full-length Aβ peptide, including 1 or 2 amino acid substitutions, were also found to be biologically active anti-angiogenics. However at low doses, Aβ appears to be pro-angiogenic (Paris, et al. 2004 Angiogenesis. 7, 75-85; Cantara, et al. 2004 F.A.S.E.B. J. 18, 1943-5).

SUMMARY OF THE INVENTION

It has been surprisingly discovered that biologically active fragments of full length Aβ peptides are useful as anti-angiogenic agents. These anti-angiogenic Aβ peptide fragments may be used to treat pathological conditions mediated by undesired and/or uncontrolled angiogenesis (characterized as "angiogenic diseases"), as described further herein.

Thus, in a first aspect, the present invention provides a variety of anti-angiogenic Aβ peptide fragments as well as compositions which include one or more such fragments. In one embodiment, the biologically active Aβ peptide fragment may be 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 or 39 amino acids in length.

In a particular embodiment, the anti-angiogenic Aβ peptide fragment is the $A\beta_{1-28}$ peptide fragment, the $A\beta_{10-35}$ peptide fragment, the $A\beta_{12-28}$ peptide fragment, the $A\beta_{13-20}$ peptide fragment, or other biologically active fragments or variants or homologs thereof.

In a specific embodiment, the anti-angiogenic Aβ peptide fragment is $A\beta_{12-28}$ and contains the amino acid sequence HHQKLVFF (SEQ ID NO:1), or biologically active fragments, variants or homologs thereof.

In another specific embodiment, the anti-angiogenic Aβ peptide fragment is $A\beta_{13-20}$ or the amino acid sequence HHQKLVFF (SEQ ID NO:1), or biologically active variants or homologs thereof. The variants may include, for example, amino acid substitutions.

In another embodiment, the present invention is a pharmaceutical composition comprising an anti-angiogenic Aβ peptide fragment and one or more pharmaceutically acceptable carriers, diluents, or excipients.

In a second aspect, the present invention provides a method for treating a disease or disorder mediated by pathological angiogenesis by administering to a subject in need thereof an effective amount of a biologically active Aβ peptide fragment, wherein the fragment is between 8 and 39 amino acids in length. The biologically active Aβ peptide fragment is optionally administered in combination or alternation with one or more therapeutic agents. The subject may be, for example, a mammal such as a human.

In one embodiment, the present invention is a method for treating cancer by administering to a subject in need thereof an effective amount of a biologically active Aβ peptide fragment, optionally, in combination or alternation with one or more chemotherapeutic agents.

In a particular embodiment, the present invention is a method of treating cancer by administering to a subject in need thereof an effective amount of a $A\beta_{12-38}$ peptide fragment containing the amino acid sequence HHQKLVFF (SEQ ID NO:1) or biologically active fragments, variants or homologs thereof.

In another particular embodiment, the method of treating cancer involves administering to a subject in need thereof an effective amount of $A\beta_{13-20}$ peptide fragment or the amino acid sequence HHQKLVFF (SEQ ID NO:1) or biologically active variants or homologs thereof.

The biologically active Aβ peptide fragment can be administered by any suitable means including, but not limited to, oral, parenteral, intravenous, intraarterial, pulmonary, mucosal, topical, transdermal, subcutaneous, intramuscular, intrathecal or intraperitoneal administration.

A third aspect of the present invention provides diagnostic methods and kits for detection and measurement of anti-angiogenic Aβ peptide fragment activity in biological fluids and tissues.

A fourth aspect of the present invention provides diagnostic methods and kits to screen for compounds that are potentially therapeutic in treatment of Alzheimer's disease by interfering with the anti-angiogenic effect of the Aβ peptide fragment.

DESCRIPTION OF DRAWINGS

FIG. 10 is a listing of sequences of A-Beta peptides and APP as well as the nucleic acids encoding them, as described in U.S. Patent Publication No. 2003/0077261 to Paris et al.

DETAILED DESCRIPTION OF THE INVENTION

Figure 1:
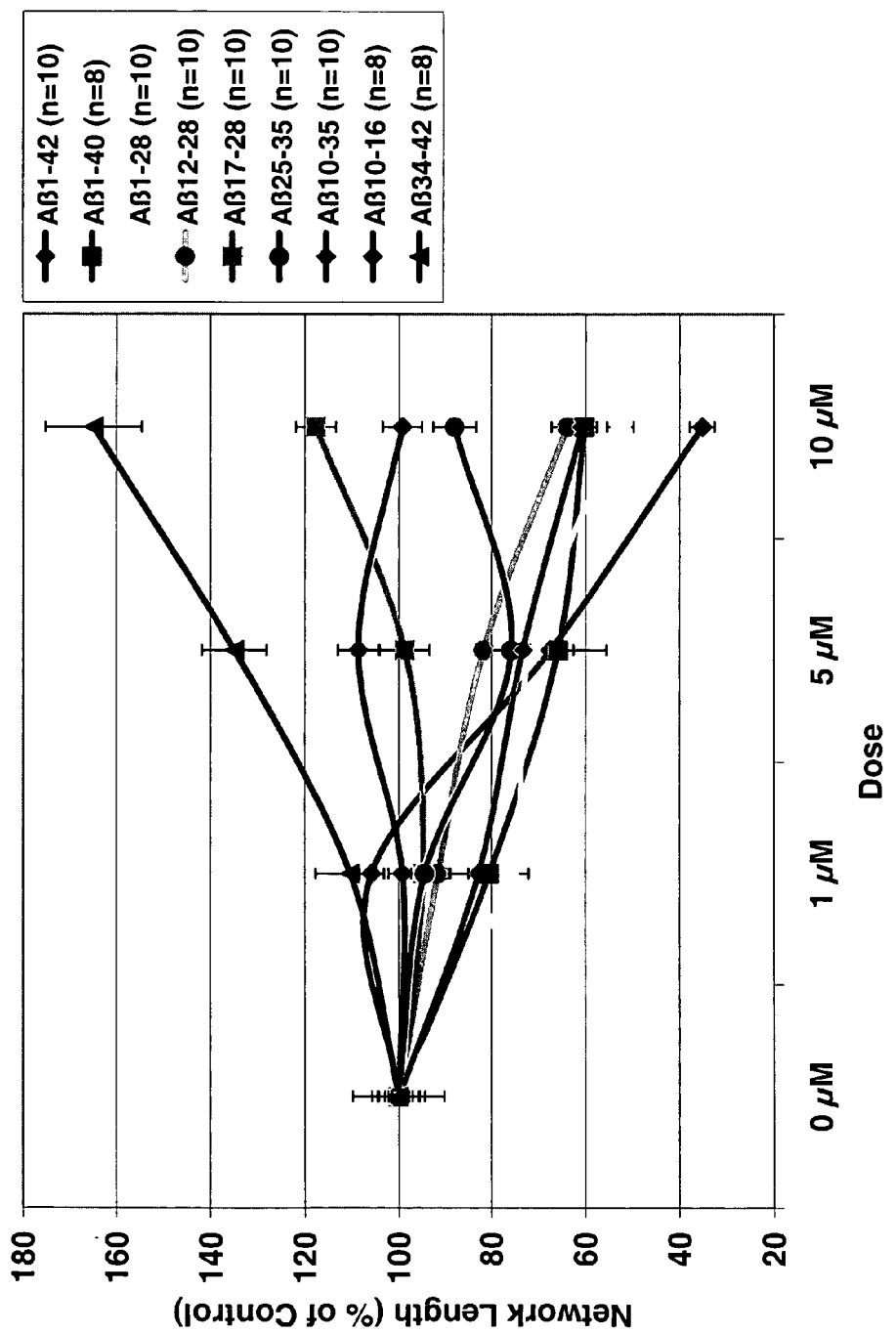
FIG. 1 is a graph of the total length of capillary tubes expressed as a percentage of control treatment for 0, 1, 5 and 10 μM doses of various Aβ peptide fragments as described in Example 8.

Anti-angiogenic therapy is an attractive approach for inhibition of tumor progression, as tumors depend upon an adequate blood supply for growth. It is disclosed herein that short peptides derived from the Aβ sequence inhibit angiogenesis, and can be used for anti-cancer therapy.

Provided are anti-angiogenic Aβ peptide fragments that can be used to treat pathological conditions mediated by undesired and/or uncontrolled or pathological angiogenesis. Provided herein is a particular anti-angiogenic motif (HHQKLVFF; (SEQ ID NO:1)) which may be used in anti-tumor or anti-angiogenic therapies.

Anti-Angiogenic Peptide Fragments

The present invention provides anti-angiogenic fragments of Aβ peptides useful for the treatment of disorders or diseases associated with pathological or unwanted angiogenesis.

The term "Aβ peptide fragment" as used herein refers to a biologically active fragment of a full length Aβ peptides (e.g., $A\beta_{1-40}$, $A\beta_{1-42}$, $A\beta_{1-43}$) and includes Aβ peptide fragment variants, homologs (such as mammalian orthologs) and isoforms, unless otherwise noted. The term also includes fragments with substitutions of one or more equivalent amino acids, or non-natural amino acids.

In one embodiment, the Aβ peptide fragment is at least one amino acid less in number than the total number of amino acids found in the full-length Aβ peptide. Full length Aβ peptides are derived from proteolytic processing of one or more isoforms of the amyloid precursor protein (APP), a transmembrane glycoprotein (Kang, J. et al. Nature (Lond.). (1987) 325: 733-736). The 39-43-amino acid-long Aβ peptide amino acid sequence begins in the ectodomain of APP and extends into the transmembrane region. Aβ is formed after sequential cleavage of APP by the β- and γ-secretases. $A\beta_{1-42}$ and $A\beta_{1-43}$ forms are specifically found in all kinds of AD plaques, indicating that those forms are critically important in AD pathology.

In a particular embodiment, the Aβ peptide fragment is at least one amino acid less in number than the total number of amino acids found in the full length $A\beta_{1-40}$ peptide. The $A\beta_{1-40}$ peptide fragment consists of, for example, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 or 39 amino acids.

In another particular embodiment, the Aβ peptide fragment is at least one amino acid less in number than the total number of amino acids found in the full length $A\beta_{1-42}$ peptide. The $A\beta_{1-42}$ fragment consists of, for example, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or 41 amino acids.

In another particular embodiment, the Aβ peptide fragment is at least one amino acid less in number than the total number of amino acids found in the full length $A\beta_{1-43}$ peptide. The $A\beta_{1-43}$ fragment consists of, for example, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 41, or 42 amino acids.

In one embodiment, the fragment consists of, for example, 8, 9, 10, 11, 12, 13, 14, 15, 16, 17, 18, 19, 20, 21, 22, 23, 24, 25, 26, 27, 28 or more amino acid residues, and includes the sequence HHQKLVFF (SEQ ID NO:1).

In one embodiment, one or more of the following biologically active Aβ peptide fragments may be used to treat diseases or disorders associated with unwanted or pathological angiogenesis: the $A\beta_{1-28}$ peptide, the $A\beta_{10-35}$ peptide, the $A\beta_{12-28}$ peptide, the $A\beta_{13-20}$ peptide, or biologically active fragments or variants thereof.

The anti-angiogenic Aβ peptide fragment preferably contains the HHQK (SEQ ID NO:9) proteoglycan binding region, since fragments without that sequence ($A\beta_{25-35}$, $A\beta_{17-28}$, and $A\beta_{34-42}$) were not active, suggesting that the heparin binding motif HHQK (SEQ ID NO:9) is required to mediate the anti-angiogenic activity of Aβ. The $A\beta_{10-16}$ fragment was inactive even though it contains the HHQK (SEQ ID NO:9) sequence, suggesting that the HHQK (SEQ ID NO:9) proteoglycan binding motif is not sufficient to inhibit angiogenesis and that other neighboring residues are required. In particular, the LVFF (SEQ ID NO:10) sequence immediately following the HHQK (SEQ ID NO:9) domain is also required for inhibition of angiogenesis. Thus, preferred Aβ peptide fragments contain the amino acid sequence HHQKLVFF (SEQ ID NO:1).

In one embodiment, the fragment consists of, for example, 8, 9, 10, 11, 12, 13, 14, 15, 16, 17, 18, 19, 20, 21, 22, 23, 24, 25, 26, 27, 28, 29, 30, 31, 32, 33, 34, 25, 36, 37, 38 or more amino acid residues, and includes the sequence HHQKLVFF (SEQ ID NO:1). Such fragments may include one or more (e.g. 2, 3 or 4) substitutions of equivalent amino acids, including, e.g., non-natural amino acids.

In one embodiment, the Aβ peptide fragment is a $A\beta_{12-28}$ peptide containing the amino acid sequence HHQKLVFF (SEQ ID NO:1), or a biologically active fragment or variant thereof.

In another embodiment, the Aβ peptide fragment is a $A\beta_{13-20}$ peptide fragment or the amino acid sequence HHQKLVFF (SEQ ID NO:1), or a biologically active fragment or variant thereof.

In another embodiment, the Aβ peptide fragment is, e.g., a 10, 20, 30, or 40 amino acid fragment of the Aβ peptide.

The peptide fragments are obtained, for example, by chemical synthesis, or are recombinantly produced by host cells.

Likewise, the terms variant and homologous are also used interchangeably. "Variant" or "homologous" peptide fragments will be understood to designate those containing, in relation to the native polypeptide sequence, modifications such as deletion, addition, or substitution of at least one amino acid, truncation, extension, or the addition of chimeric heterologous polypeptides. Optionally, "variant" or "homologous" peptide fragments can contain a mutation or post-translational modifications.

Among the "variant" or "homologous" polypeptides or peptide fragments, those whose amino acid sequence exhibits 80.0% to 99.9% (inclusive) identity to the native polypeptide sequence are preferred. These percentages are purely statistical and differences between two peptide sequences can be distributed randomly and over the entire sequence length.

"Variant" or "homologous" polypeptide sequences exhibiting a percentage identity with the polypeptides of the present invention can, alternatively, have 80, 81, 82, 83, 84, 85, 86, 87, 88, 89, 90, 91, 92, 93, 94, 95, 96, 97, 98, or 99 percent identity with the polypeptide sequences of the instant invention. The expression equivalent amino acid is intended here to designate any amino acid capable of being substituted for one of the amino acids in the basic structure without, however, essentially modifying the biological activities of the corresponding peptides and as provided below.

Several substitutions could be made to HHQKLVFF (SEQ ID NO:1) (motif) region of Aβ while potentially retaining the substitution antiangiogenic properties of the peptide. Specifically, the following expression indicates such equivalent substitutions for HHQKLVFF (SEQ ID NO:1):

[RH]-H-[NQ]-[RK]-[ILV]-[ILV]-F-F;            (SEQ ID NO: 11)

Exemplary sequences with such motifs are listed in Table 1. Sources are noted if a particular peptide sequence is a part of a naturally occurring protein.

TABLE 1

| Amino acid sequence | Source, if naturally-occurring |
|---|---|
| HHQKLVFF (SEQ ID NO: 1) | human APP/Aβ |
| RHQKLVFF (SEQ ID NO: 12) | rat/mouse APP/Aβ |
| HHNKLVFF (SEQ ID NO: 13) | |
| RHNKLVFF (SEQ ID NO: 14) | |
| HHQRLVFF (SEQ ID NO: 15) | |
| RHQRLVFF (SEQ ID NO: 16) | |
| HHNRLVFF (SEQ ID NO: 17) | |
| RHNRLVFF (SEQ ID NO: 18) | |
| HHQKIVFF (SEQ ID NO: 19) | |
| RHQKIVFF (SEQ ID NO: 20) | |

TABLE 1-continued

| Amino acid sequence | Source, if naturally-occurring |
|---|---|
| HHNKIVFF (SEQ ID NO: 21) | |
| RHNKIVFF (SEQ ID NO: 22) | |
| HHQRIVFF (SEQ ID NO: 23) | |
| RHQRIVFF (SEQ ID NO: 24) | tr:Q3YB12_BACST putative regulator [*Geobacillus stearothermophilus*] |
| HHNRIVFF (SEQ ID NO: 25) | |
| RHNRIVFF (SEQ ID NO: 26) | |
| HHQKVVFF (SEQ ID NO: 27) | |
| RHQKVVFF (SEQ ID NO: 28) | |
| HHNKVVFF (SEQ ID NO: 29) | |
| RHNKVVFF (SEQ ID NO: 30) | |
| HHQRVVFF (SEQ ID NO: 31) | [Q6CET0] *Yarrowia lipolytica* chromosome B of strain CLIB99 of *Yarrowia lipolytica* (trembl). |
| RHQRVVFF (SEQ ID NO: 32) | |
| HHNRVVFF (SEQ ID NO: 33) | |
| RHNRVVFF (SEQ ID NO: 34) | |
| HHQKLIFF (SEQ ID NO: 35) | |
| RHQKLIFF (SEQ ID NO: 36) | |
| HHNKLIFF (SEQ ID NO: 37) | |
| RHNKLIFF (SEQ ID NO: 38) | |
| HHQRLIFF (SEQ ID NO: 39) | |
| RHQRLIFF (SEQ ID NO: 40) | |
| HHNRLIFF (SEQ ID NO: 41) | |
| RHNRLIFF (SEQ ID NO: 42) | |
| HHQKIIFF (SEQ ID NO: 43) | |
| RHQKIIFF (SEQ ID NO: 44) | |
| HHNKIIFF (SEQ ID NO: 45) | |
| RHNKIIFF (SEQ ID NO: 46) | |
| HHQRIIFF (SEQ ID NO: 47) | |
| RHQRIIFF (SEQ ID NO: 48) | |
| HHNRIIFF (SEQ ID NO: 49) | |
| RHNRIIFF (SEQ ID NO: 50) | |
| HHQKVIFF (SEQ ID NO: 51) | |
| RHQKVIFF (SEQ ID NO: 52) | |
| HHNKVIFF (SEQ ID NO: 53) | |
| RHNKVIFF (SEQ ID NO: 54) | |
| HHQRVIFF (SEQ ID NO: 55) | |
| RHQRVIFF (SEQ ID NO: 56) | |
| HHQKLLFF (SEQ ID NO: 57) | |
| RHQKLLFF (SEQ ID NO: 58) | |
| HHNKLLFF (SEQ ID NO: 59) | |
| RHNKLLFF (SEQ ID NO: 60) | |
| HHQRLLFF (SEQ ID NO: 61) | |
| RHQRLLFF (SEQ ID NO: 62) | |
| HHNRLLFF (SEQ ID NO: 63) | |
| RHNRLLFF (SEQ ID NO: 64) | Trembl sequence entry tr:Q7QS20_GIALA |
| HHQKILFF (SEQ ID NO: 65) | |
| RHQKILFF (SEQ ID NO: 66) | |
| HHNKILFF (SEQ ID NO: 67) | |
| RHNKILFF (SEQ ID NO: 68) | |
| HHQRILFF (SEQ ID NO: 69) | |
| RHQRILFF (SEQ ID NO: 70) | |
| HHNRILFF (SEQ ID NO: 71) | |
| RHNRILFF (SEQ ID NO: 72) | |
| HHQKVLFF (SEQ ID NO: 73) | |
| RHQKVLFF (SEQ ID NO: 74) | |
| HHNKVLFF (SEQ ID NO: 75) | |
| RHNKVLFF (SEQ ID NO: 76) | |
| HHQRVLFF (SEQ ID NO: 77) | |
| RHQRVLFF (SEQ ID NO: 78) | |
| HHNRVIFF (SEQ ID NO: 79) | |
| RHNRVIFF (SEQ ID NO: 80) | |

The motif search from http://motif.genome.jp/MOTIF2.html was used to search the peptide combinations in the NR-AA Trembl/Swissprot database. The substitution of physico-chemical equivalent amino acids in peptide sequences is known in the art. (Eisenberg, et al. 1984 "Amino acid scale: Normalized consensus hydrophobicity scale." J. Mol. Biol. 179:125-142; and Mathura, et al. 2001, "New quantitative descriptors for amino acids based on multidimensional scaling of a large number of physical-chemical properties", J. Mol. Modeling. 7:445-453).

In one embodiment, the Aβ peptide fragment consists of or comprises one of the peptide sequences listed in Table 1, with optional equivalent amino acid substitutions.

The subject invention also provides biologically active peptide fragments capable of eliciting an immune response. The immune response can provide components (either antibodies or components of the cellular immune response (e.g., B-cells, helper, cytotoxic, and/or suppressor T-cells) reactive with the peptide fragment.

Fragments, as described herein, can be obtained by cleaving a polypeptide with a proteolytic enzyme (such as trypsin, chymotrypsin, or collagenase) or with a chemical reagent, such as cyanogen bromide (CNBr). Alternatively, polypeptide fragments can be generated in a highly acidic environment, for example at pH 2.5. Such polypeptide fragments may be also prepared by chemical synthesis or using hosts transformed with an expression vector containing nucleic acids encoding polypeptide fragments. The transformed host cells contain a nucleic acid and are cultured according to well-known methods; thus, expression of these fragments is possible, under the control of appropriate elements for regulation and/or expression.

The peptides can be modified by variation in the splicing of transcriptional products of the Aβ gene, genetic recombination, or by chemical synthesis. Such peptides can contain at least one modification in relation to the polypeptide sequence being modified. These modifications can include the addition, substitution, deletion of amino acids contained within the polypeptides.

Conservative substitutions whereby an amino acid of one class is replaced with another amino acid of the same type fall within the scope of the subject invention so long as the substitution does not materially alter the biological activity of the polypeptide. For example, the class of nonpolar amino acids include Ala, Val, Leu, Ile, Pro, Met, Phe, Gly and Trp; the class of uncharged polar amino acids include Ser, Thr, Cys, Tyr, Asn, and Gln; the class of acidic amino acids includes Asp and Glu; and the class of basic amino acids includes Lys, Arg, and His. In some instances, non-conservative substitutions can be made where these substitutions do not significantly detract from the biological activity of the polypeptide.

In order to extend the life of the polypeptides provided, it may be advantageous to use non-natural amino acids, for example in the D form, or alternatively amino acid analogs, such as sulfur-containing forms of amino acids. Alternative means for increasing the life of polypeptides can also be used. For example, peptides fragments can be recombinantly modified to include elements that increase the plasma, or serum half-life. These elements include, and are not limited to, antibody constant regions (see for example, U.S. Pat. No. 5,565,335, hereby incorporated by reference in its entirety, including all references cited therein), or other elements such as those disclosed in U.S. Pat. Nos. 6,319,691; 6,277,375; or 5,643,570, each of which is incorporated by reference in its entirety, including all references cited within each respective patent. Alternatively, the polynucleotides and genes can be recombinantly fused to elements that are useful in the preparation of immunogenic constructs for the purposes of vaccine formulation or elements useful for the isolation of the polypeptides provided.

The peptide fragments disclosed may further contain linkers that facilitate the attachment of the fragments to a carrier molecule for delivery or diagnostic purposes. The linkers can also be used to attach fragments to solid support matrices for use in affinity purification protocols. In one embodiment, the linkers specifically exclude where the fragment is a subsequence of another peptide, polypeptide, or protein as identified in a search of protein sequence databases. In other words, the non-identical portions of the other peptide, polypeptide, of protein is not considered to be a "linker" in this aspect. Non-limiting examples of "linkers" suitable for the practice of the invention include chemical linkers (such as those sold by Pierce, Rockford, Ill.), peptides that allow for the connection of the immunogenic fragment to a carrier molecule (see, for example, linkers disclosed in U.S. Pat. Nos. 6,121,424; 5,843,464; 5,750,352; and 5,990,275, hereby incorporated by reference in their entirety). In various embodiments, the linkers can be up to 50 amino acids in length, up to 40 amino acids in length, up to 30 amino acids in length, up to 20 amino acids in length, up to 10 amino acids in length, or up to 5 amino acids in length.

In other specific embodiments, the peptides may be expressed as a fusion, or chimeric protein product (joined via a peptide bond to a heterologous protein sequence (e.g., a different protein)). Such a chimeric product can be made by ligating the appropriate nucleic acid sequences encoding the desired amino acid sequences to each other by methods known in the art, in the proper coding frame, and expressing the chimeric product by methods commonly known in the art (see, for example, U.S. Pat. No. 6,342,362, hereby incorporated by reference in its entirety; Altendorf, et al. 1999-WWW, 2000 "Structure and Function of the $F_o$ Complex of the ATP Synthase from *Escherichia Coli*," J. of Experimental Biology 203:19-28, G. B.; Baneyx 1999 Biotechnology 10:411-21; Eihauer, et al. 2001 J. Biochem. Biophys. Methods 49:455-65; Jones, et al. 1995 J. Chromatography 707:3-22; Jones, et al. 1995 J. of Chromatography A. 707:3-22; Margolin, et al. 2000 Methods 20:62-72; Puig, et al. 2001 Methods 24:218-29; Sassenfeld, et al. 1990 Tib. Tech. 8:88-93; Sheibani, et al. 1999 Prep. Biochem. & Biotechnol. 29(1):77-90; Skerra, et al. 1999 Biomolecular Engineering 16:79-86; Smith, et al. 1998 The Scientist 12(22):20; Smyth, et al. 2000 Methods in Molecular Biology, 139:49-57; Unger, et al. 1997 The Scientist 11(17):20; each of which is hereby incorporated by reference in their entireties). Alternatively, such a chimeric product may be made by protein synthetic techniques, e.g., by use of a peptide synthesizer. Fusion peptides can comprise polypeptides and one or more protein transduction domains, as described above. Such fusion peptides are particularly useful for delivering the cargo polypeptide through the cell membrane.

Increasing the amount of Aβ peptide fragment activity within a tissue is useful in treating a variety of angiogenic diseases, such as cancers, tumors, and/or malignancies. Thus, according to the methods provided, the amount of Aβ peptide fragment activity can be increased within a tissue by directly administering the Aβ peptide fragment to a patient suffering from an angiogenic disease (such as exogenous delivery of the Aβ peptide fragment) or by indirect or genetic means (such as delivery of a polynucleotide encoding the Aβ peptide fragment or upregulating the endogenous Aβ peptide fragment activity). Non-limiting examples of such cancers, tumors, and/or malignancies that can be treated using the methods of the invention include prostate cancer, breast cancer, melanoma, chronic myelogenous leukemia, cervical cancer, adenocarcinomas, lymphoblastic leukemia, colorectal cancer, and lung carcinoma.

The peptide fragments or nucleic acids encoding them can be used in screening, or aiding in the diagnosis of, an individual suspected of having an angiogenic or angiogenesis-mediated disease. The peptide fragments disclosed herein and nucleic acids encoding them can be used to detect the Aβ peptide in hybridization assays by the use of complementary sequences. The presence of a significantly increased amount of Aβ peptide fragment is associated with an indication of Alzheimer's disease. The presence of a significantly decreased amount of Aβ peptide is associated with an indication of an angiogenic disease, such as a malignancy or cancer. Aβ gene product can be detected by well-known methodologies including, and not limited to, Western blots, enzyme linked immunoassays (ELISAs), radioimmunoassays (RIAs), Northern blots, Southern blots, PCR-based assays, or other assays for the quantification of gene product known to the skilled artisan. This information, in conjunction with other information available to the skilled practitioner, assists in making a diagnosis.

In one aspect, the subject invention concerns a method of inhibiting angiogenesis in a patient in need of anti-angiogenesis therapy by administration of biologically active Aβ peptide fragment to the patient.

In one embodiment, a treatment for a pathological condition selected from the group consisting of cancer, arthritis, atherosclerosis, psoriasis, macular degeneration, and diabetic retinopathy by administering to the patient a therapeutically effective amount of an Aβ peptide fragment.

In one embodiment, biologically active variants of the Aβ peptide fragments are utilized, wherein the variants have a substitution at the 21 amino acid position, or the 22 amino acid position, or 23 amino acid position, or combinations thereof. In a specific embodiment, the substitution(s) is a conservative substitution which does not materially alter the biological activity of the polypeptide.

Various means for delivering polypeptides to a cell can be utilized to carry out the methods provided. For example, protein transduction domains (PTDs) can be fused to the polypeptide, producing a fusion polypeptide, in which the PTDs are capable of transducing the polypeptide cargo across the plasma membrane (Wadia, J. S, and Dowdy, S. F., Curr. Opin. Biotechnol. 2002, 13(1), 52-56). Examples of PTDs include the *Drosophila* homeotic transcription protein antennapedia (Antp), the herpes simples virus structural protein VP22, and the human immuno-deficiency virus 1 (HIV-1) transcriptional activator Tat protein.

According to the method of angiogenesis inhibition provided, recombinant cells can be administered to a patient, wherein the recombinant cells have been genetically modified to express Aβ peptide fragments disclosed herein.

The method of angiogenesis inhibition provided can be used to treat a patient suffering from cancer, or as a cancer preventative. The method of tumor inhibition provided can be used to treat patients suffering from a variety of cancers including, but not limited to, cancer of the breast, prostate, melanoma, chronic myelogenous leukemia, cervical cancer, adenocarcinoma, lymphoblastic leukemia, colorectal cancer, and lung carcinoma. According to the methods provided, various other anti-cancer or anti-tumor compounds, such as cytotoxic agents, can be administered in conjunction with Aβ peptide fragments.

Nucleotide Sequences Encoding Aβ Fragments

In another aspect, the subject invention provides isolated and/or purified nucleotide sequences comprising a polynucleotide sequence encoding the amino acid sequence of the peptide fragments disclosed herein.

Also provided are isolated nucleic acid molecules comprising polynucleotides encoding the Aβ peptide fragments. One aspect of the invention provides isolated nucleic acid molecules comprising polynucleotides having a nucleotide sequence selected from the group consisting of: (a) a nucleotide sequence encoding any of the amino acid sequences of the polypeptides described herein including in Table 1; and (b) a nucleotide sequence complementary to any of the nucleotide sequences in (a).

Further embodiments of the invention include isolated nucleic acid molecules that comprise a polynucleotide having a nucleotide sequence at least 90% identical, and more preferably at least 95%, 96%, 97%, 98% or 99% identical to any of the nucleotide sequences in (a) or (b) above.

Nucleotide, polynucleotide, or nucleic acid sequences(s) are understood to mean, according to the present invention, either a double-stranded DNA, a single-stranded DNA, or products of transcription of the said DNAs (e.g., RNA molecules). The nucleic acid, polynucleotide, or nucleotide sequences can be isolated, purified (or partially purified), by separation methods including, but not limited to, ion-exchange chromatography, molecular size exclusion chromatography, affinity chromatography, or by genetic engineering methods such as amplification, cloning or subcloning.

Optionally, the polynucleotide sequences can also contain one or more polynucleotides encoding heterologous polypeptide sequences (e.g., tags that facilitate purification of the polypeptides of the invention (see, for example, U.S. Pat. No. 6,342,362, hereby incorporated by reference in its entirety; Altendorf, et al. 1999-WWW, 2000 "Structure and Function of the $F_o$ Complex of the ATP Synthase from *Escherichia Coli*," J. of Experimental Biology 203:19-28, G. B.; Baneyx 1999 Biotechnology 10:411-21; Eihauer, et al. 2001 J. Biochem. Biophys. Methods 49:455-65; Jones, et al. 1995 J. Chromatography 707:3-22; Jones, et al. 1995 J. of Chromatography A. 707:3-22; Margolin, et al. 2000 Methods 20:62-72; Puig, et al. 2001 Methods 24:218-29; Sassenfeld, et al. 1990 Tib. Tech. 8:88-93; Sheibani, et al. 1999 Prep. Biochem. & Biotechnol. 29(1):77-90; Skerra, et al. 1999 Biomolecular Engineering 16:79-86; Smith, et al. 1998 The Scientist 12(22):20; Smyth, et al. 2000 Methods in Molecular Biology, 139:49-57; Unger, et al. 1997 The Scientist 11(17): 20; each of which is hereby incorporated by reference in their entireties), or commercially available tags from vendors such as such as STRATAGENE (La Jolla, Calif.), NOVAGEN (Madison, Wis.), QIAGEN, Inc., (Valencia, Calif.), or INVITROGEN (San Diego, Calif.).

Vectors

Other aspects provide vectors containing one or more of the polynucleotides provided, such as vectors containing nucleotides encoding biologically active Aβ peptide fragments. The vectors can be vaccine, replication, or amplification vectors. In some embodiments, the polynucleotides are operably associated with regulatory elements capable of causing the expression of the polynucleotide sequences. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations of the aforementioned vector sources, such as those derived from plasmid and bacteriophage genetic elements (e.g., cosmids and phagemids).

As indicated above, vectors can also comprise elements necessary to provide for the expression and/or the secretion of a polypeptide, such as a fragment of the Aβ peptide, encoded by the nucleotide sequences provided in a given host cell. The vector can contain one or more elements selected from the group consisting of a promoter, signals for initiation of translation, signals for termination of translation, and appropriate regions for regulation of transcription. In certain embodiments, the vectors can be stably maintained in the host cell and can, optionally, contain signal sequences directing the secretion of translated protein. Other embodiments provide vectors that are not stable in transformed host cells. Vectors can integrate into the host genome or be autonomously-replicating vectors.

In a specific embodiment, a vector comprises a promoter operably linked to a protein or peptide-encoding nucleic acid sequence, one or more origins of replication, and, optionally, one or more selectable markers (e.g., an antibiotic resistance gene). Non-limiting exemplary vectors for the expression of polypeptides include pBr-type vectors, pET-type plasmid vectors (PROMEGA), pBAD plasmid vectors (INVITROGEN) or those provided in the examples below. Furthermore, vectors are useful for transforming host cells for the cloning or expression of the nucleotide sequences provided.

Promoters which may be used to control expression include, but are not limited to, the CMV promoter, the SV40 early promoter region (Bernoist and Chambon 1981 Nature 290:304-310), the promoter contained in the 3' long terminal repeat of Rous sarcoma virus (Yamamoto, et al. 1980 Cell 22:787-797), the herpes thymidine kinase promoter (Wagner et al. 1981 Proc. Natl. Acad. Sci. USA 78:1441-1445), the regulatory sequences of the metallothionein gene (Brinster et al. 1982 Nature 296:39-42); prokaryotic vectors containing promoters such as the β-lactamase promoter (Villa-Kamaroff, et al. 1978 Proc. Natl. Acad. Sci. USA 75:3727-3731), or the tac promoter (DeBoer, et al. 1983 Proc. Natl. Acad. Sci. USA 80:21-25); see also, "Useful Proteins from Recombinant Bacteria" in Scientific American, 1980, 242:74-94; plant expression vectors comprising the nopaline synthetase promoter region (Herrera-Estrella et al. 1983 Nature 303:209-213) or the cauliflower mosaic virus 35S RNA promoter (Gardner, et al. Nucl. Acids Res. 9:2871), and the promoter of the photosynthetic enzyme ribulose biphosphate carboxylase (Herrera-Estrella et al. 1984 Nature 310:115-120); promoter elements from yeast or fungi such as the Gal 4 promoter, the ADC (alcohol dehydrogenase) promoter, PGK (phosphoglycerol kinase) promoter, and/or the alkaline phosphatase promoter.

Homologous Nucleotide Sequences

Provided herein are "homologous" or "modified" nucleotide sequences. Modified nucleic acid sequences will be understood to mean any nucleotide sequence obtained by mutagenesis according to techniques well known to persons skilled in the art, and exhibiting modifications in relation to the normal sequences. For example, mutations in the regulatory and/or promoter sequences for the expression of a polypeptide that result in a modification of the level of expression of a polypeptide provide for a "modified nucleotide sequence". Likewise, substitutions, deletions, or additions of nucleic acid to the polynucleotides provide for "homologous" or "modified" nucleotide sequences. In various embodiments, "homologous" or "modified" nucleic acid sequences have substantially the same biological or serological activity as the native (naturally occurring) Aβ peptide fragments. A "homologous" or "modified" nucleotide sequence will also be understood to mean a splice variant of the polynucleotides of the instant invention or any nucleotide sequence encoding a "modified polypeptide" as defined below.

A homologous nucleotide sequence, as described herein, encompasses a nucleotide sequence having a percentage identity with the bases of the nucleotide sequences of between at least (or at least about) 80.0% to 99.9% (inclusive), or 85% to 99%, or 90% to 99%, or 95% to 99%.

In various embodiments, homologous sequences exhibiting a percentage identity with the bases of the nucleotide sequences described can have 80, 81, 82, 83, 84, 85, 86, 87, 88, 89, 90, 91, 92, 93, 94, 95, 96, 97, 98, or 99 percent identity with the polynucleotide sequences of the instant invention.

Both protein and nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman 1988 Proc. Natl. Acad. Sci. U.S.A. 85(8):2444-2448; Altschul, et al. 1990 J. Mol. Biol. 215(3): 403-410; Thompson, et al. 1994 Nucleic Acids Res. 22(2): 4673-4680; Higgins, et al. 1996 Methods Enzymol. 266:383-402; Altschul, et al. 1990 J. Mol. Biol. 215(3):403-410; Altschul, et al. 1993 Nature Genetics 3:266-272).

Also provided are nucleotide sequences complementary to any of the polynucleotide sequences disclosed herein. Thus, the invention is understood to include any DNA whose nucleotides are complementary to those of the sequence of the invention, and whose orientation is reversed (e.g., an antisense sequence).

Further provided are fragments of the polynucleotide sequences disclosed herein. Representative fragments of the polynucleotide sequences will be understood to mean any nucleotide fragment having at least 8 or 9 successive nucleotides, preferably at least 12 successive nucleotides, and still more preferably at least 15 or at least 20 successive nucleotides of the sequence from which it is derived. The upper limit for such fragments is the total number of polynucleotides found in the sequence encoding for $A\beta_{1-42}$ peptide, (or, in certain embodiments, the open reading frame (ORF) identified herein). The appropriate fragments thereof encoding for a specific peptide are also useful. For example, nucleotide sequences that are Aβ peptide fragment homologs, or fragments thereof, which have been previously identified, can be utilized to carry out the method for inhibiting angiogenesis of the subject invention.

Hybridization and Detection Probes

Among these representative fragments, those capable of hybridizing under stringent conditions with a nucleotide sequence are preferred. Conditions of high or intermediate stringency are provided infra and are chosen to allow for hybridization between two complementary DNA fragments. Hybridization conditions for a polynucleotide of about 300 bases in size will be adapted by persons skilled in the art for larger- or smaller-sized oligonucleotides, according to methods well known in the art (see, for example, Sambrook, et al. 1989 Molecular Cloning, A Laboratory Manual, Second Edition, Cold Spring Harbor Press, N.Y., pp. 9.47-9.57).

Also provided are detection probes (e.g., fragments of the disclosed polynucleotide sequences) for hybridization with a target sequence or an amplicon generated from the target sequence. Such a detection probe will advantageously have as sequence a sequence of at least 9, 12, 15, 20, 25, 30, 35, 40, 45, 50, 55, 60, 65, 70, 75, 80, 85, 90, 95, or 100 nucleotides. Alternatively, detection probes can comprise 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127 and up to, for example, 128 consecutive nucleotides of the disclosed nucleic acids. The detection probes can also be used as labeled probe or primer in the subject invention. Labeled probes or primers are labeled with a radioactive compound or with another type of label. Alternatively, non-labeled nucleotide sequences may be used directly as probes or primers; however, the sequences are generally labeled with a radioactive element ($^{32}$P, $^{35}$S, $^{3}$H, $^{125}$I) or with a molecule such as biotin, acetylaminofluorene, digoxigenin, 5-bromo-deoxyuridine, or fluorescein to provide probes that can be used in numerous applications.

The nucleotide sequences disclosed may also be used in analytical systems, such as DNA chips. DNA chips and their uses are well known in the art and (see for example, U.S. Pat. Nos. 5,561,071; 5,753,439; 6,214,545; Schena, et al. 1996 BioEssays 18:427-431; Bianchi, et al. 1997 Clin. Diagn.

Virol. 8:199-208; each of which is hereby incorporated by reference in their entireties) and/or are provided by commercial vendors such as AFFYMETRIX, Inc. (Santa Clara, Calif.).

Various degrees of stringency of hybridization can be employed. The more severe the conditions, the greater the complementarity that is required for duplex formation. Severity of conditions can be controlled by temperature, probe concentration, probe length, ionic strength, time, and the like. Preferably, hybridization is conducted under moderate to high stringency conditions by techniques well known in the art, as described, for example, in Keller, G. H., M. M. Manak 1987 DNA Probes, Stockton Press, New York, N.Y., pp. 169-170.

By way of example, hybridization of immobilized DNA on Southern blots with $^{32}$P-labeled gene-specific probes can be performed by standard methods (Maniatis, et al. 1982 Molecular Cloning: A Laboratory Manual, Cold Spring Harbor Laboratory, New York). In general, hybridization and subsequent washes can be carried out under moderate to high stringency conditions that allow for detection of target sequences with homology to the exemplified polynucleotide sequence. For double-stranded DNA gene probes, hybridization can be carried out overnight at 20-25° C. below the melting temperature (Tm) of the DNA hybrid in 6×SSPE, 5×Denhardt's solution, 0.1% SDS, 0.1 mg/ml denatured DNA. The melting temperature is described by the following formula (Beltz et al. 1983 Methods of Enzymology, R. Wu, L. Grossman and K. Moldave [eds.] Academic Press, New York 100:266-285).

$$T_m = 81.5° C. + 16.6 \log [Na+] + 0.41 (\% G+C) - 0.61 (\% \text{formamide}) - 600/\text{length of duplex in base pairs.}$$

Washes are typically carried out as follows:

(1) twice at room temperature for 15 minutes in 1×SSPE, 0.1% SDS (low stringency wash);

(2) once at $T_m$ −20° C. for 15 minutes in 0.2×SSPE, 0.1% SDS (moderate stringency wash).

For oligonucleotide probes, hybridization can be carried out overnight at 10-20° C. below the melting temperature ($T_m$) of the hybrid in 6×SSPE, 5×Denhardt's solution, 0.1% SDS, 0.1 mg/ml denatured DNA. $T_m$ for oligonucleotide probes can be determined by the following formula:

$$T_m (° C.) = 2(\text{number } T/A \text{ base pairs}) + 4(\text{number } G/C \text{ base pairs})$$

(Suggs et al. ICN-UCLA Symp. Dev. Biol. Using Purified Genes, D. D. Brown [ed.], Academic Press, New York, 23:683-693).

Washes can be carried out as follows:

(1) twice at room temperature for 15 minutes 1×SSPE, 0.1% SDS (low stringency wash;

2) once at the hybridization temperature for 15 minutes in 1×SSPE, 0.1% SDS (moderate stringency wash).

In general, salt and/or temperature can be altered to change stringency. With a labeled DNA fragment >70 or so bases in length, the following conditions can be used:

1 Low: 1 or 2×SSPE, room temperature Low: 1 or 2×SSPE, 42° C. Moderate: 0.2× or 1×SSPE, 65° C. High: 0.1×SSPE, 65° C.

By way of another non-limiting example, procedures using conditions of high stringency can also be performed as follows: Pre-hybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C., the preferred hybridization temperature, in pre-hybridization mixture containing 100 µg/ml denatured salmon sperm DNA and 5-20×10$^6$ cpm of $^{32}$P-labeled probe. Alternatively, the hybridization step can be performed at 65° C. in the presence of SSC buffer, 1×SSC corresponding to 0.15M NaCl and 0.05 M Na citrate. Subsequently, filter washes can be done at 37° C. for 1 h in a solution containing 2×SSC, 0.01% PVP, 0.01% Ficoll, and 0.01% BSA, followed by a wash in 0.1×SSC at 50° C. for 45 min. Alternatively, filter washes can be performed in a solution containing 2×SSC and 0.1% SDS, or 0.5×SSC and 0.1% SDS, or 0.1×SSC and 0.1% SDS at 68° C. for 15 minute intervals. Following the wash steps, the hybridized probes are detectable by autoradiography. Other conditions of high stringency which may be used are well known in the art (see, for example, Sambrook, et al. 1989 Molecular Cloning, A Laboratory Manual, Second Edition, Cold Spring Harbor Press, N.Y., pp. 9.47-9.57; and Ausubel, et al. 1989 Current Protocols in Molecular Biology, Green Publishing Associates and Wiley Interscience, N.Y., each incorporated herein in its entirety).

A further non-limiting example of procedures using conditions of intermediate stringency are as follows: Filters containing DNA are pre-hybridized, and then hybridized at a temperature of 60° C. in the presence of a 5×SSC buffer and labeled probe. Subsequently, filters washes are performed in a solution containing 2×SSC at 50.degree. C. and the hybridized probes are detectable by autoradiography. Other conditions of intermediate stringency which may be used are well known in the art (see, for example, Sambrook et al. 1989 Molecular Cloning, A Laboratory Manual, Second Edition, Cold Spring Harbor Press, N.Y., pp. 9.47-9.57; and Ausubel et al 1989 Current Protocols in Molecular Biology, Green Publishing Associates and Wiley Interscience, N.Y., each of which is incorporated herein in its entirety).

Duplex formation and stability depend on substantial complementarity between the two strands of a hybrid and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions and deletions can be produced in a given polynucleotide sequence in many ways, and these methods are known to an ordinarily skilled artisan. Other methods may become known in the future.

It is also well known in the art that restriction enzymes can be used to obtain functional fragments of the subject DNA sequences. For example, Bal31 exonuclease can be conveniently used for time-controlled limited digestion of DNA (commonly referred to as "erase-a-base" procedures). See, for example, Maniatis, et al. 1982 Molecular Cloning: A Laboratory Manual, Cold Spring Harbor Laboratory, New York; Wei, et al. 1983 J. Biol. Chem. 258:13006-13512. The nucleic acid sequences disclosed can also be used as molecular weight markers in nucleic acid analysis procedures.

Host Cells

Provided are host cells transformed by a polynucleotide according to the invention and the production of Aβ peptide fragments by the transformed host cells. In some embodiments, transformed cells comprise an expression vector containing polynucleotide sequences for an Aβ peptide fragment. Other embodiments provide for host cells transformed with nucleic acids. Yet other embodiments provide transformed cells comprising an expression vector containing fragments of Aβ polynucleotide sequences. Transformed host cells can be cultured under conditions allowing the replication and/or the expression of the nucleotide sequences provided. Expressed polypeptides are recovered from culture media and purified, for further use, according to methods known in the art.

The host cell may be chosen from eukaryotic or prokaryotic systems, for example bacterial cells (Gram negative or Gram positive), yeast cells, animal cells, plant cells, and/or insect cells using baculovirus vectors. In some embodiments, the host cell for expression of the polypeptides include, and are not limited to, those taught in U.S. Pat. Nos. 6,319,691; 6,277,375; 5,643,570; 5,565,335; Unger, et al. 1997 The Scientist 11(17):20; or Smith, et al. 1998 The Scientist 12(22): 20, each of which is incorporated by reference in its entirety, including all references cited within each respective patent or reference. Other exemplary, and non-limiting, host cells include *Staphylococcus* spp., *Enterococcus* spp., *E. coli*, and *Bacillus subtilis*; fungal cells, such as *Streptomyces* spp., *Aspergillus* spp., *S. cerevisiae, Schizosaccharomyces pombe, Pichia pastoris, Hansela polymorpha, Kluveromyces lactis,* and *Yarrowia lipolytica*; insect cells such as *Drosophila* S2 and *Spodoptera* Sf9 cells; animal cells such as CHO, COS, HeLa, C127, 3T3, BHK, 293 and Bowes melanoma cells; and plant cells. A great variety of expression systems can be used to produce the polypeptides provided and polynucleotides can be modified according to methods known in the art to provide optimal codon usage for expression in a particular expression system.

Furthermore, a host cell strain may be chosen that modulates the expression of the inserted sequences, modifies the gene product, and/or processes the gene product in the specific fashion. Expression from certain promoters can be elevated in the presence of certain inducers; thus, expression of the genetically engineered polypeptide may be controlled. Furthermore, different host cells have characteristic and specific mechanisms for the translational and post-translational processing and modification (e.g., glycosylation, phosphorylation) of proteins. Appropriate cell lines or host systems can be chosen to ensure the desired modification and processing of the foreign protein expressed. For example, expression in a bacterial system can be used to produce an unglycosylated core protein product whereas expression in yeast will produce a glycosylated product. Expression in mammalian cells can be used to provide "native" glycosylation of a heterologous protein. Furthermore, different vector/host expression systems may effect processing reactions to different extents.

Nucleic acids and/or vectors can be introduced into host cells by well-known methods, such as, calcium phosphate transfection, DEAE-dextran mediated transfection, transfection, microinjection, cationic lipid-mediated transfection, electroporation, transduction, scrape loading, ballistic introduction and infection (see, for example, Sambrook, et al. 1989 Molecular Cloning: A Laboratory Manual, 2.sup.nd Ed., Cold Spring Harbor Laboratory Press, Cold Spring Harbor, N.Y.).

The subject invention also provides for the expression of a polypeptide, derivative, or a variant (e.g., a splice variant) encoded by a polynucleotide sequence disclosed herein. Alternatively, the invention provides for the expression of a polypeptide fragment obtained from a polypeptide, derivative, or a variant encoded by a polynucleotide fragment derived from the polynucleotide sequences disclosed herein. In either embodiment, the disclosed sequences can be regulated by a second nucleic acid sequence so that the polypeptide or fragment is expressed in a host transformed with a recombinant DNA molecule according to the subject invention. For example, expression of a protein or peptide may be controlled by any promoter/enhancer element known in the art.

The subject invention also provides nucleic acid-based methods for the identification of the presence of the Aβ gene, or fragments or variants thereof, in a sample. These methods can utilize the nucleic acids provided and are well known to those skilled in the art (see, for example, Sambrook, et al. 1989 Molecular Cloning, A Laboratory Manual, Second Edition, Cold Spring Harbor Press, N.Y., pp. 9.47-9.57, or Abbaszadega, et al. 2001 Reviews in Biology and Biotechnology, 1(2):21-26). Among the techniques useful in such methods are enzymatic gene amplification (or PCR), Southern blots, Northern blots, or other techniques utilizing nucleic acid hybridization for the identification of polynucleotide sequences in a sample. The nucleic acids can be used to screen individuals for disorders associated with dysregulation of the Aβ gene or its transcriptional products.

The subject invention also provides polypeptides encoded by nucleotide sequences of the invention. The subject invention also provides fragments of at least 5 amino acids of a polypeptide encoded by the polynucleotides of the instant invention.

Pharmaceutical Formulations and Administration

As used herein, the term "administration" or "administering" refers to the process of delivering an agent to a patient. The process of administration can be varied, depending on the agent, or agents, and the desired effect. Administration can be accomplished by any means appropriate for the therapeutic agent, for example, by oral, parenteral, mucosal, pulmonary, topical, catheter-based, rectal, intracranial, intracerebroventricular, intracerebral, intravaginal or intrauterine delivery. Parenteral delivery can include for example, subcutaneous intravenous, intramuscular, intra-arterial, and injection into the tissue of an organ, particularly tumor tissue. Mucosal delivery can include, for example, intranasal delivery. Oral or intranasal delivery can include the administration of a propellant. Pulmonary delivery can include inhalation of the agent. Catheter-based delivery can include delivery by iontropheretic catheter-based delivery. Oral delivery can include delivery of a coated pill, or administration of a liquid by mouth. Administration can generally also include delivery with a pharmaceutically acceptable carrier, such as, for example, a buffer, a polypeptide, a peptide, a polysaccharide conjugate, a liposome, and/or a lipid. Gene therapy protocol is also considered an administration in which the therapeutic agent is a polynucleotide capable of accomplishing a therapeutic goal when expressed as a transcript or a polypeptide into the patient.

In one embodiment, the Aβ peptide fragment is administered in an effective amount to inhibit pathological angiogenesis. As used herein, the term "angiogenesis" is intended to refer to the process by which new blood vessels are formed and which is essential to a variety of normal body activities (such as reproduction, development, and wound repair). The process is believed to involve a complex interplay of molecules which both stimulate and inhibit the growth of endothelial cells, the primary cells of the capillary blood vessels. Under normal conditions, these molecules appear to maintain the microvasculature in a quiescent state (i.e., one of no capillary growth) for prolonged periods. When necessary, however (such as during wound repair), these cells can undergo rapid proliferation and turnover within a short period of time. Although angiogenesis is a highly regulated process under normal conditions, many conditions (characterized as "angiogenic diseases") are driven by persistent unregulated angiogenesis. Otherwise stated, unregulated angiogenesis may either cause a particular pathological condition directly or exacerbate an existing pathological condition. For example, ocular neovascularization has been implicated as the most common cause of blindness and dominates approximately twenty eye diseases. In certain existing conditions, such as arthritis, newly formed capillary blood vessels invade the joints and destroy cartilage. In diabetes, new capillaries formed in the retina invade the vitreous, bleed, and cause blindness. Growth and metastasis of tumors are also angiogensis-dependent (Folkman, J., Cancer Research, 46:467-473, 1986; Folkman, J., Journal of the National Cancer Institute, 82:4-6, 1989). It has been shown, for example, that tumors which enlarge to greater than 2 mm, must obtain their own blood supply and do so by inducing the growth of new capillary blood vessels. Once these new blood vessels become embedded in the tumor, they provide a means for tumor cells to enter the circulation and metastasize to distant site, such as liver, lung or bone (Weidner, N. et al., The New England Journal of Medicine, 324(1):1-8, 1991).

The pharmaceutical compositions of the subject invention can be formulated according to known methods for preparing pharmaceutically useful compositions. Formulations are described in a number of sources which are well known and readily available to those skilled in the art. For example, Remington's Pharmaceutical Sciences (Martin E W 1995 Easton Pa. Mack Publishing Company, 19.sup.th ed.) describes formulations which can be used in connection with the subject invention. Formulations suitable for parenteral administration include, for example, aqueous sterile injection solutions, which may contain antioxidants, buffers, bacteriostats, and solutes which render the formulation isotonic with the blood of the intended recipient; and aqueous and non-aqueous sterile suspensions which may include suspending agents and thickening agents. The formulations maybe presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question.

In one embodiment, the Aβ peptide fragments are delivered in a sustained release formulation. The formulations provide extended release and extended half-life. Controlled release systems suitable for use include, without limitation, diffusion-controlled, solvent-controlled and chemically-controlled systems. Diffusion controlled systems include, for example reservoir devices, in which the Aβ peptide fragment or fragments are enclosed within a device such that release of the peptide fragments is controlled by permeation through a diffusion barrier. Common reservoir devices include, for example, membranes, capsules, microcapsules, liposomes, and hollow fibers. Monolithic (matrix) device are a second type of diffusion controlled system, wherein the Aβ peptide fragment(s) are dispersed or dissolved in an rate-controlling matrix (e.g., a polymer matrix). The peptide fragments are homogeneously dispersed throughout a rate-controlling matrix and the rate of drug release is controlled by diffusion through the matrix. Polymers suitable for use in the monolithic matrix device include naturally occurring polymers, synthetic polymers and synthetically modified natural polymers, as well as polymer derivatives.

Therapeutically effective and optimal dosage ranges for the Aβ peptide fragments can be determined using methods known in the art. Guidance as to appropriate dosages to achieve an anti-angiogenesis and/or anti-tumor effect is provided from the exemplified assays disclosed herein. The minimal amounts of Aβ peptide fragment to achieve a therapeutic effect can likewise be determined. In one embodiment, the Aβ peptide fragment is administered in an equivalent amount to be within the μM dose range. In another embodiment, an amount equivalent to about 1 μM to about 100 μM Aβ peptide fragment is administered. In another embodiment, an amount equivalent to about 2 μM to about 10 μM Aβ peptide fragment is administered.

The subject invention also pertains to diagnostic and/or screening methods and kits to screen for compounds that are potentially therapeutic in treatment of Alzheimer's disease by interfering with the anti-angiogenic effect of an Aβ peptide fragment.

In one aspect, included is a method for identifying compounds that interfere with Aβ-induced angiogenesis inhibition, wherein the method includes the steps of (a) contacting a first biological sample capable of undergoing angiogenesis with a test compound, a biologically active amount of an Aβ peptide fragment, and an angiogenic agent; and (b) determining the extent of angiogenesis that occurs in the first biological sample. Optionally, the method can include the steps of: (c) separately contacting a second biological sample capable of undergoing angiogenesis with a biologically active amount of an Aβ peptide fragment and an angiogenic agent; (d) determining the extent of angiogenesis that occurs in the second biological sample; and (e) comparing the extent of angiogenesis that occurs in the first biological sample with that which occurs in the second biological sample. In this way, steps (c)-(d) can be utilized as a control. Preferably, the same Aβ peptide fragment is used in the first and second biological samples.

Determining the extent of angiogenesis can be carried out using methods known in the art, such as those described herein, and can be done qualitatively or quantitatively. For example, molecular or cellular markers of cancer or tumor growth can be utilized. The extent of angiogenesis can also be determined by measuring the amount of endothelial cell proliferation or the extent of blood vessel growth within a biological sample.

The biological samples utilized in the methods and kits can include various biological fluids and tissues that can exhibit angiogenesis and/or tumor development. For example, the biological sample can be arterial tissue, corneal tissue, endothelial cells, umbilical cord tissue, chorionic allantoid membrane, and the like.

The angiogenic agent can be any molecule, compound, or cell that is capable of inducing angiogenesis in the biological sample. For example, the angiogenic agent can be a trophic factor, such as a neurotrophic factor. The angiogenic factor can be a cytokine or growth factor such as vascular endothelial growth factor, platelet-derived growth factor, and basic fibroblast growth factor. The diagnostic and/or screening methods of the subject invention can be carried out in vivo, such as in an animal model, or in vitro.

In another aspect, the subject invention includes a kit for identifying compounds that interfere with Aβ-induced angiogenesis inhibition. The kit can include a compartment containing at least one Aβ peptide fragment and, optionally, a compartment containing an angiogenic agent. Furthermore, the kit can optionally include a compartment containing one or more biological samples.

In another aspect, a method is provided for identifying compounds that interfere with Aβ-induced anti-tumor activity, including the steps of: (a) contacting a first tumor tissue with a test compound and a biologically active amount of an Aβ peptide fragment; and (b) determining the extent of tumor growth that occurs in the tumor tissue. Optionally, the method can further include the steps of: (c) separately contacting a second tumor tissue with a biologically active amount of an Aβ peptide fragment; (d) determining the extent of tumor growth that occurs in the second tumor tissue; and (e) comparing the extent of tumor growth that occurs in the first tumor tissue with that which occurs in the second tumor tissue. In this way, steps (c)-(d) can be utilized as a control. The extent of tumor growth can be determined quantitatively or qualitatively using methods known in the art, including methods described herein. For example, molecular or cellular markers of cancer or tumor growth can be utilized.

In another aspect, the subject invention includes a kit for identifying compounds that interfere with Aβ-induced antitumor activity. The kit can include a compartment containing at least one Aβ peptide fragment and, optionally, a compartment containing at least one tumor tissue. Furthermore, the kit can optionally include a compartment containing one or more biological samples.

The test compounds that can be screened using the methods and kits of the subject invention can include any substance, agent, or molecule, including, for example, small molecules and living or dead cells.

A variety of patients may be treated including any vertebrate species. Preferably, the patient is of a mammalian species. Mammalian species which benefit from the disclosed methods of treatment include, and are not limited to, apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales.

Treatment of Tumors and Cancer

In one embodiment, a method for treating tumors, cancers or other proliferative disorders in animals or humans in need of such treatment is provided, comprising administering a therapeutically effective amount, optionally in unit dosage form, of an Aβ peptide fragment described herein. Also provided are methods for inhibiting angiogenesis in animals or humans in need thereof, comprising administering a therapeutically effective amount, optionally in unit dosage form, of a an Aβ peptide fragment disclosed herein.

Aβ peptide fragments and pharmaceutical compositions comprising the fragments, are provided, that can be used in one embodiment to treat tumors and cancers, including, but not limited to cancers or tumors in the following tissues or organs: breast, prostate, lung, bronchus, colon, urinary tract, bladder, kidney, pancreas, thyroid, stomach, brain, esophagus, liver, intrahepatic bile duct, cervix, skin, larynx, heart, testis, small intestine, thyroid, vulva, gallbladder, pleura, eye, nose, ear, nasopharynx, ureter, gastrointestinal system, rectal tissue, pancreas, head and neck. Cancers that can be treated include without limitation non-Hodgkin lymphoma, melanoma, multiple myeloma, acute myeloid leukemia, chronic lymphatic leukemia, Hodgkin lymphoma, chronic myeloid leukemia, acute lymphatic leukemia, carcinomas, adenocarcinomas; sarcomas; lymphomas, and leukemias.

In one subembodiment, the Aβ peptide fragments can be used to treat, for example, prostate cancer, lung cancer, colorectal cancer, bladder cancer, cutaneous melanoma, pancreatic cancer, leukemia, breast cancer, endometrial cancer, non-Hodgkin's lymphoma, and ovarian cancer.

In another subembodiment, the Aβ peptide fragments can be used to treat epithelial cell cancers and tumors including: skin cancer, cervical cancer, anal carcinoma, esophageal cancer, hepatocellular carcinoma (in the liver), laryngeal cancer, renal cell carcinoma (in the kidneys), stomach cancer, testicular cancers, and thyroid cancer.

In another subembodiment, the Aβ peptide fragments are used to treat hematological malignancies (blood and bone marrow) including leukemia, lymphoma, and multiple myeloma.

In a further subembodiment, the Aβ peptide fragments are used to treat sarcomas including: osteosarcoma (in bone), chondrosarcoma (arising from cartilage), and rhabdomyosarcoma (in muscle).

In another subembodiment, the Aβ peptide fragments are used to treat cancers and tumors of miscellaneous origin including: brain tumors, gastrointestinal stromal tumors (GIST), mesothelioma (in the pleura or pericardium), thymoma and teratomas, and melanoma.

Examples of tumors that can be treated include, without limitation, malignant brain tumors, such as glioblastomas; malignant lung tumors, such as adenocarcinomas; or malignant tumors of the breast, colon, kidney, bladder, head or neck.

Proliferative disorders that can be treated include, without limitation, hematopoietic disorders, such as leukemias, lymphomas or polycythemias; and ocular disorders, such as diabetic retinopathy, macular degeneration, glaucoma or retinitis pigmentosa. Inflammatory disorders that can be treated include, without limitation, rheumatoid arthritis, osteoarthritis, pulmonary fibrosis, sarcoid granulomas, psoriasis or asthma.

In one embodiment, the Aβ peptide fragments can be used to treat a carcinoma, sarcoma, lymphoma, leukemia, and/or myeloma. In other embodiments, the Aβ peptide fragments disclosed herein can be used to treat solid tumors.

In other embodiments, the Aβ peptide fragments described herein can be used for the treatment of cancer, including, but not limited to the cancers listed in Table 2a below.

TABLE 2a

| Types of Cancer | |
|---|---|
| Acute Lymphoblastic Leukemia, Adult | Hairy Cell Leukemia |
| Acute Lymphoblastic Leukemia, Childhood | Head and Neck Cancer |
| | Hepatocellular (Liver) Cancer, Adult (Primary) |
| Acute Myeloid Leukemia, Adult | |
| Acute Myeloid Leukemia, Childhood | Hepatocellular (Liver) Cancer, Childhood (Primary) |
| Adrenocortical Carcinoma | |
| Adrenocortical Carcinoma, Childhood | Hodgkin's Lymphoma, Adult |
| AIDS-Related Cancers | Hodgkin's Lymphoma, Childhood |
| AIDS-Related Lymphoma | Hodgkin's Lymphoma During Pregnancy |
| Anal Cancer | Hypopharyngeal Cancer |

TABLE 2a-continued

Types of Cancer

Astrocytoma, Childhood Cerebellar
Astrocytoma, Childhood Cerebral
Basal Cell Carcinoma
Bile Duct Cancer, Extrahepatic
Bladder Cancer
Bladder Cancer, Childhood
Bone Cancer, Osteosarcoma/Malignant Fibrous Histiocytoma
Brain Stem Glioma, Childhood
Brain Tumor, Adult
Brain Tumor, Brain Stem Glioma, Childhood
Brain Tumor, Cerebellar Astrocytoma, Childhood
Brain Tumor, Cerebral Astrocytoma/Malignant Glioma, Childhood
Brain Tumor, Ependymoma, Childhood
Brain Tumor, Medulloblastoma, Childhood
Brain Tumor, Supratentorial Primitive Neuroectodermal Tumors, Childhood
Brain Tumor, Visual Pathway and Hypothalamic Glioma, Childhood
Brain Tumor, Childhood
Breast Cancer
Breast Cancer, Childhood
Breast Cancer, Male
Bronchial Adenomas/Carcinoids, Childhood
Burkitt's Lymphoma
Carcinoid Tumor, Childhood
Carcinoid Tumor, Gastrointesiinal
Carcinoma of Unknown Primary
Central Nervous System Lymphoma, Primary
Cerebellar Astrocytoma, Childhood
Cerebral Astrocytoma/Malignant Glioma, Childhood
Cervical Cancer
Childhood Cancers
Chronic Lymphocytic Leukemia
Chronic Myelogenous Leukemia
Chronic Myeloproliferative Disorders
Colon Cancer
Colorectal Cancer, Childhood
Cutaneous T-Cell Lymphoma, see Mycosis Fungoides and Sezary Syndrome
Endometrial Cancer
Ependymoma, Childhood
Esophageal Cancer
Esophageal Cancer, Childhood
Ewing's Family of Tumors
Extracranial Germ Cell Tumor, Childhood
Extragonadal Germ Cell Tumor
Extrahepatic Bile Duct Cancer
Eye Cancer, Intraocular Melanoma
Eye Cancer, Retinoblastoma
Gallbladder Cancer
Gastric (Stomach) Cancer
Gastric (Stomach) Cancer, Childhood
Gastrointestinal Carcinoid Tumor
Germ Cell Tumor, Extracranial, Childhood
Germ Cell Tumor, Extragonadal
Germ Cell Tumor, Ovarian
Gestational Trophoblastic Tumor
Glioma, Adult
Glioma, Childhood Brain Stem
Glioma, Childhood Cerebral Astrocytoma
Glioma, Childhood Visual Pathway and Hypothalamic Skin Cancer (Melanoma)
Skin Carcinoma, Merkel Cell
Small Cell Lung Cancer
Small Intestine Cancer
Soft Tissue Sarcoma, Adult Hypothalamic and Visual Pathway Glioma, Childhood
Intraocular Melanoma
Islet Cell Carcinoma (Endocrine Pancreas)
Kaposi's Sarcoma
Kidney (Renal Cell) Cancer
Kidney Cancer, Childhood
Laryngeal Cancer
Laryngeal Cancer, Childhood
Leukemia, Acute Lymphoblastic, Adult
Leukemia, Acute Lymphoblastic, Childhood
Leukemia, Acute Myeloid, Adult
Leukemia, Acute Myeloid, Childhood
Leukemia, Chronic Lymphocytic
Leukemia, Chronic Myelogenous
Leukemia, Hairy Cell
Lip and Oral Cavity Cancer
Liver Cancer, Adult (Primary)
Liver Cancer, Childhood (Primary)
Lung Cancer, Non-Small Cell
Lung Cancer, Small Cell
Lymphoma, AIDS-Related
Lymphoma, Burkitt's
Lymphoma, Cutaneous T-Cell, see Mycosis Fungoides and Sézary Syndrome
Lymphoma, Hodgkin's, Adult
Lymphoma, Hodgkin's, Childhood
Lymphoma, Hodgkin's During Pregnancy
Lymphoma, Non-Hodgkin's, Adult
Lymphoma, Non-Hodgkin's, Childhood
Lymphoma, Non-Hodgkin's During Pregnancy
Lymphoma, Primary Central Nervous System
Macroglobulinemia, Waldenstrtöm's
Malignant Fibrous Histiocytoma of Bone/Osteosarcoma
Medulloblastoma, Childhood
Melanoma
Melanoma, Intraocular (Eye)
Merkel Cell Carcinoma
Mesothelioma, Adult Malignant
Mesothelioma, Childhood
Metastatic Squamous Neck Cancer with Occult Primary
Multiple Endocrine Neoplasia Syndrome, Childhood
Multiple Myeloma/Plasma Cell Neoplasm
Mycosis Fungoides
Myelodysplastic Syndromes
Myelodysplastic/Myeloproliferative Diseases
Myelogenous Leukemia, Chronic
Myeloid Leukemia, Adult Acute
Myeloid Leukemia, Childhood Acute
Myeloma, Multiple
Myeloproliferative Disorders, Chronic
Nasal Cavity and Paranasal Sinus Cancer
Nasopharyngeal Cancer
Nasopharyngeal Cancer, Childhood
Neuroblastoma
Non-Hodgkin's Lymphoma, Adult
Non-Hodgkin's Lymphoma, Childhood
Non-Hodgkin's Lymphoma During Pregnancy
Non-Small Cell Lung Cancer
Oral Cancer, Childhood
Oral Cavity Cancer, Lip and
Oropharyngeal Cancer
Osteosarcoma/Malignant Fibrous Histiocytoma of Bone
Ovarian Cancer, Childhood
Ovarian Epithelial Cancer

TABLE 2a-continued

| Types of Cancer | |
|---|---|
| Soft Tissue Sarcoma, Childhood | Ovarian Germ Cell Tumor |
| Squamous Cell Carcinoma, see Skin Cancer (non-Melanoma) | Ovarian Low Malignant Potential Tumor |
| Squamous Neck Cancer with Occult Primary, Metastatic | Pancreatic Cancer |
| | Pancreatic Cancer, Childhood |
| Stomach (Gastric) Cancer | Pancreatic Cancer, Islet Cell |
| Stomach (Gastric) Cancer, Childhood | Paranasal Sinus and Nasal Cavity Cancer |
| Supratentorial Primitive Neuroectodermal Tumors, Childhood | Parathyroid Cancer |
| | Penile Cancer |
| T-Cell Lymphoma, Cutaneous, see Mycosis Fungoides and Sezary Syndrome | Pheochromocytoma |
| | Pineoblastoma and Supratentorial Primitive Neuroectodermal Tumors, Childhood |
| Testicular Cancer | |
| Thymoma, Childhood | Pituitary Tumor |
| Thymoma and Thymic Carcinoma | Plasma Cell Neoplasm/Multiple Myeloma |
| Thyroid Cancer | |
| Thyroid Cancer, Childhood | Pleuropulmonary Blastoma |
| Transitional Cell Cancer of the Renal Pelvis and Ureter | Pregnancy and Breast Cancer |
| | Pregnancy and Hodgkin's Lymphoma |
| Trophoblastic Tumor, Gestational | Pregnancy and Non-Hodgkin's Lymphoma |
| Unknown Primary Site, Carcinoma of, Adult | |
| | Primary Central Nervous System Lymphoma |
| Unknown Primary Site, Cancer of, Childhood | |
| | Prostate Cancer |
| Unusual Cancers of Childhood | Rectal Cancer |
| Ureter and Renal Pelvis, Transitional Cell Cancer | Renal Cell (Kidney) Cancer |
| | Renal Cell (Kidney) Cancer, Childhood |
| Urethral Cancer | Renal Pelvis and Ureter, Transitional Cell Cancer |
| Uterine Cancer, Endometrial | |
| Uterine Sarcoma | Retinoblastoma |
| Vaginal Cancer | Rhabdomyosarcoma, Childhood |
| Visual Pathway and Hypothalamic Glioma, Childhood | Salivary Gland Cancer |
| | Salivary Gland Cancer, Childhood |
| Vulvar Cancer | Sarcoma, Ewing's Family of Tumors |
| Waldenström's Macroglobulinemia | Sarcoma, Kaposi's |
| Wilms' Tumor | Sarcoma, Soft Tissue, Adult |
| | Sarcoma, Soft Tissue, Childhood |
| | Sarcoma, Uterine |
| | Sezary Syndrome |
| | Skin Cancer (non-Melanoma) |
| | Skin Cancer, Childhood |

Anti-Angiogenic Activity of the Aβ Peptide Fragment

Without being limited to any theory, it is possible that the sequence HHQKLVFF (SEQ ID NO:1) is the sequence of Aβ that confers anti-angiogenic activity.

Numerous studies have shown that heparin and various proteoglycans on the cell surface can bind to Aβ peptides (Snow, et al. 1995 Arch. Biochem. Biophys. 320, 84-95; McLaurin, et al. 2000 Eur. J. Biochem. 267, 6353-61; McKeon J, Holland L A. 2004 Electrophoresis 25, 1243-8), and heparan sulfate proteoglycans have been shown to be associated with amyloid deposits in AD brain (van Horssen, et al. 2001 Acta Neuropathol. (Berl). 102, 604-14). Heparin sulfate proteoglycans also play a prominent role during angiogenesis by allowing the interaction of specific growth factors such as basic fibroblast growth factor (bFGF) and vascular endothelial growth factor (VEGF) with the cell surface. In this way, proteoglycans are thought to modulate the interaction of growth factors with receptors (Rusnati M, Presta M. 1996 Int. J. Clin. Lab. Res. 26, 15-23; Dougher, et al. 1997 Growth Factors. 14, 257-68). It is shown herein that the addition of exogenous heparin is able to effectively reverse the anti-angiogenic activity of $A\beta_{1-42}$. Addition of heparin alone caused a slight inhibition of angiogenesis, which is consistent with studies indicating the inhibitory effect of excess heparins on angiogenesis. The mechanism of this effect has been suggested to be via an increased release of tissue factor pathway inhibitor (Mousa S A, Mohamed S. 2004 Thromb. Haemost. 92, 627-33).

Cell surface proteoglycans such as heparan sulfate proteoglycans can bind to and allow the activity of various growth factors including VEGF and bFGF (Iozzo R V, San Antonio J D. 2001 J. Clin. Invest. 108, 349-55; Presta, et al. 2005 Cytokine Growth Factor Rev. 16, 159-78; Sanderson, et al. 2005 J. Cell Biochem. September 7, (advance electronic publication)). It is possible that Aβ binds to these proteoglycans, impacting the binding and interaction of growth factors with the cell. Therefore, as the angiogenesis assays contain heparin binding growth factors, the addition of excess heparin may act to bind out Aβ peptides and prevent their binding to the cell surface, hence opposing the anti-angiogenic activity of Aβ. Alternatively, Aβ has also been shown to directly interact with the heparin binding motif on VEGF (Yang, et al. 2005 J. Neurochem. 93, 118-27); hence it is possible that the binding of Aβ to heparin can prevent it from binding to VEGF, reversing the anti-angiogenic activity of Aβ. It is also possible that heparin (and other glycosaminoglycans) affect the conformational properties of Aβ peptides, changing the rate of fibril formation (Castillo, et al. 1999 J. Neurochem. 72, 1681-7; Cohlberg, et al. 2002 Biochemistry. 41, 1502-11) thereby rendering the peptide unable to block angiogenesis. The anti-angiogenic activity of Aβ peptides in-vitro seems to be related to their conformational properties, as preparations of Aβ containing higher β-sheet content are more potently anti-angiogenic (Gebbink, et al. 2000 Biochim. Biophys. Acta. 1502, 16-30. Additionally, soluble oligomers of the peptide are particularly anti-angiogenic whereas fibrillar forms are inactive (Paris, et al. 2005 Brain Res. Mol. Brain. Res. 136, 212-30; Skovseth, et al. 2005 Blood 105, 1044-51) suggesting that particular residues in the Aβ peptide need to be exposed in order to inhibit angiogenesis.

One motif within the Aβ peptide sequence which may be important for imparting anti-angiogenic activity is the putative proteoglycan binding region, HHQK (Cardin, A. D.; Weintaub, H. J. R. 1989 Arteriosclerosis. 9, 21-32; Snow, et al. 1995 Arch. Biochem. Biophys. 320, 84-95; McLaurin, et al. 2000 Eur. J. Biochem. 267, 6353-61; McKeon, et al. 2004 Electrophoresis. 25, 1243-8). Proteoglycans are known to play a regulatory role during angiogenesis (Moon, et al. 2005 J. Cell Physiol. 203, 166-76; Tkachenko, et al. 2005 Circ. Res. 96, 488-500; Presta, et al. 2005) Cytokine Growth Factor Rev. 16, 159-78). Also, numerous studies have indicated an important role for heparan sulfate proteoglycans in AD pathogenesis, and it has been suggested that interference with the binding of these molecules to Aβ may be beneficial therapeutically (Leveugle, et al. 1994) Neuroreport. 5, 1389-92; Kisilevsky, et al. 2002 J. Mol. Neurosci. 19, 45-50).

Another potentially significant sequence for anti-angiogenic activity is the four amino acids adjacent to the HHQK (SEQ ID NO:9) motif, towards the C-terminal portion (LVFF) (SEQ ID NO:10). This region is known to constitute part of the β strand and hence is important for oligomerization of the peptide (Morimoto, et al. 2004 J. Biol. Chem. 279, 52781-8; Irie, et al. 2005 J. Biosci. Bioeng. 99, 437-47). It has recently been shown in a conformational model of $Aβ_{10-42}$ that the highly hydrophobic residues 17-20 are exposed in the dimeric form, while studies by another group reveal that this region is buried in the fibrillar form (Mathura, et al. 2005 Biochem. Biophys. Res. Commun. 332, 585-92; Olofsson, et al. 2005 J. Biol. Chem. October 7, (advance electronic publication)).

To further investigate the possibility that Aβ could be acting by preventing the binding of growth factors to proteoglycans on the cell surface, three residues were substituted in the putative proteoglycan binding sequence, HHQK (SEQ ID NO:9) of $Aβ_{12-28}$ (SEQ ID NO:8). It is shown herein that the neutral amino acid substitutions GGQG (SEQ ID NO:81) or AAQA (SEQ ID NO:82) in place of the wildtype HHQK (SEQ ID NO:9) completely abolish the anti-angiogenic affect of the wildtype $Aβ_{12-28}$ peptide. Further, the anti-angiogenic potency of $Aβ_{12-28}$ in-vivo was confirmed by using a rat corneal micro-pocket model of VEGF-induced angiogenesis. Levels of VEGF are increased in the brain of AD patients (Kalaria, et al. 1998 Brain Res. Mol. Brain. Res. 62, 101-5; Tarkowski, et al. 2002 Neurobiol Aging. 23, 237-43), but this is not associated with an increased brain vascularization (Buee, et al. 1997 Ann. N.Y. Acad. Sci. 826, 7-24). The accumulation of Aβ in AD brains may therefore result in the inhibition of VEGF activity. VEGF is neurotrophic, it is important for maintaining vascular integrity, and also a key factor in vascular remodeling following stroke or head injury (Slevin, et al. 2000 Neuroreport 11, 2759-64; Shore, et al. 2004 Neurosurgery. 54, 605-12). The antagonistic action of Aβ towards VEGF in the AD brain may explain why AD patients and transgenic mouse models of AD do poorly following stroke (Koistinaho, et al. 2002 Proc. Natl. Acad. Sci. U.S.A. 99, 1610-5; Wen, et al. 2004 J. Biol. Chem. 279, 22684-92; Koistinaho M, Koistinaho J. 2005 Brain Res. Brain Res. Rev. 48, 240-50).

Examples provided herein support that the proteoglycan binding motif alone may not be sufficient to elicit anti-angiogenic effects, and that the amino acids immediately adjacent to this sequence (LVFF) are required to mediate the anti-angiogenic activity of Aβ. In a conformational model of Aβ oligomers, it has been shown that the LVFF sequence (amino acids 17-20) is an exposed region of the peptide (Mathura, et al. 2005 Biochem. Biophys. Res. Commun. 332, 585-92).

The pro-angiogenic affects of $Aβ_{34-42}$ have also been noted. The pro-angiogenic activity of the $Aβ_{34-42}$ fragment observed in the network assay described herein is consistent with the pro-angiogenic activity of $Aβ_{1-40/42}$ peptides at low concentrations that has previously observed (Paris, et al. 2004 Angiogenesis. 7, 75-85; Cantara, et al. 2004 F.A.S.E.B. J. 18, 1943-5). The folding of Aβ may be such that the C-terminal 34-42 sequence is left exposed when monomers and dimers are formed. Subsequently this region may be buried upon higher order oligomer or fibril formation. A recent NMR study of $Aβ_{1-42}$ fibrils confirmed that the residues 28-42 are solvent inaccessible and the back bone amides were not amenable for a deuterium exchange even after a long time period (Olofsson, et al. 2005 J. Biol. Chem. October 7, (advance electronic publication)). Thus, the pro-angiogenic effect of $Aβ_{1-40/42}$ peptides at low concentrations may be due to their predominantly monomeric or dimeric states exposing a pro-angiogenic motif (Olofsson, et al. 2005 J. Biol. Chem. October 7, (advance electronic publication); Fraser, et al. 1994 J. Mol. Biol. 244, 64-73; van Horssen, et al. 2001 Acta Neuropathol. (Berl). 102, 604-14; Rusnati, M; Presta, M. 1996 Int. J. Clin. Lab. Res. 26, 15-23; Dougher, et al. 1997 Growth Factors. 14, 257-68; Mousa, et al. 2004 Thromb. Haemost. 92, 627-33; Iozzo, et al. 2001 J. Clin. Invest. 108, 349-55; Presta, et al. 2005 Cytokine Growth Factor Rev. 16, 159-78; Sanderson, et al. 2005 J. Cell Biochem. September 7, (advance electronic publication)) in the C-terminal region.

Combination Therapy

In one aspect, the peptide fragments disclosed herein can be used in combination with at least one additional chemotherapeutic agent in order to treat a cancer, tumor or other proliferative disorder. The additional agents can be administered in combination or alternation with the compounds disclosed herein. The drugs can form part of the same composition, or be provided as a separate composition for administration at the same time or a different time.

Examples of second therapeutic agents include but are not limited to, IL-12, retinoids, interferons, angiostatin, endostatin, thalidomide, thrombospondin-1, thrombospondin-2, captopryl, anti-neoplastic agents such as alpha interferon, COMP (cyclophosphamide, vincristine, methotrexate and prednisone), etoposide, MBACOD (methortrexate, bleomycin, doxorubicin, cyclophosphamide, vincristine and dexamethasone), PRO-MACE/MOPP (prednisone, methotrexate (w/leucovin rescue), doxorubicin, cyclophosphamide, taxol, etoposide/mechlorethamine, vincristine, prednisone and procarbazine), vincristine, vinblastine, angioinhibins, TNP-470, pentosan polysulfate, platelet factor 4, angiostatin, LM-609, SU-101, CM-101, Techgalan, thalidomide, SP-PG and radiation.

Other example include agents with antimitotic effects (antimitotic inhibitors), such as those which target cytoskeletal elements, including microtubule modulators such as taxane drugs (such as taxol, paclitaxel, taxotere, docetaxel), podophylotoxins or vinca alkaloids (vincristine, vinblastine); antimetabolite drugs (such as 5-fluorouracil, cytarabine, gemcitabine, purine analogues such as pentostatin, methotrexate); alkylating agents or nitrogen mustards (such as nitrosoureas, cyclophosphamide or ifosphamide); drugs which target DNA such as the antracycline drugs adriamycin, doxorubicin, pharmorubicin or epirubicin; drugs which target topoisomerases (topoisomerase inhibitors) such as etoposide; hormones and hormone agonists or antagonists such as estrogens, antiestrogens (tamoxifen and related compounds) and androgens, flutamide, leuprorelin, goserelin, cyproterone or octreotide;

drugs which target signal transduction in tumor cells including antibody derivatives such as herceptin; alkylating drugs such as platinum drugs (cis-platin, carbonplatin, oxaliplatin, paraplatin) or nitrosoureas; drugs potentially affecting metastasis of tumours such as matrix metalloproteinase inhibitors; gene therapy and antisense agents; antibody therapeutics; other bioactive compounds of marine origin, such as the didemnins such as aplidine; corticosteroids; steroid analogues, such as dexamethasone; anti-inflammatory drugs, including nonsteroidal agents (such as acetaminophen or ibuprofen) or steroids and their derivatives in particular dexamethasone; and anti-emetic drugs, including 5HT-3 inhibitors (such as granisetron or ondansetron).

Other examples of second therapeutic agents include those disclosed below in Table 1a.

TABLE 1a

| Chemotherapeutic Agents | |
|---|---|
| 13-cis-Retinoic Acid | Neosar |
| 2-Amino-6-Mercaptopurine | Neulasta |
| 2-CdA | Neumega |
| 2-Chlorodeoxyadenosine | Neupogen |
| 5-fluorouracil | Nilandron |
| 5-FU | Nilutamide |
| 6-TG | Nitrogen Mustard |
| 6-Thioguanine | Novaldex |
| 6-Mercaptopurine | Novantrone |
| 6-MP | Octreotide |
| Accutane | Octreotide acetate |
| Actinomycin-D | Oncospar |
| Adriamycin | Oncovin |
| Adrucil | Ontak |
| Agrylin | Onxal |
| Ala-Cort | Oprevelkin |
| Aldesleukin | Orapred |
| Alemtuzumab | Orasone |
| Alitretinoin | Oxaliplatin |
| Alkaban-AQ | Paclitaxel |
| Alkeran | Pamidronate |
| All-transretinoic acid | Panretin |
| Alpha interferon | Paraplatin |
| Altretamine | Pediapred |
| Amethopterin | PEG Interferon |
| Amifostine | Pegaspargase |
| Aminoglutethimide | Pegfilgrastim |
| Anagrelide | PEG-INTRON |
| Anandron | PEG-L-asparaginase |
| Anastrozole | Phenylalanine Mustard |
| Arabinosylcytosine | Platinol |
| Ara-C | Platinol-AQ |
| Aranesp | Prednisolone |
| Aredia | Prednisone |
| Arimidex | Prelone |
| Aromasin | Procarbazine |
| Arsenic trioxide | PROCRIT |
| Asparaginase | Proleukin |
| ATRA | Prolifeprospan 20 with Carmustine implant |
| Avastin | Purinethol |
| BCG | Raloxifene |
| BCNU | Rheumatrex |
| Bevacizumab | Rituxan |
| Bexarotene | Rituximab |
| Bicalutamide | Roveron-A (interferon alfa-2a) |
| BiCNU | Rubex |
| Blenoxane | Rubidomycin hydrochloride |
| Bleomycin | Sandostatin |
| Bortezomib | Sandostatin LAR |
| Busulfan | Sargramostim |
| Busulfex | Solu-Cortef |
| C225 | Solu-Medrol |
| Calcium Leucovorin | STI-571 |
| Campath | Streptozocin |
| Camptosar | Tamoxifen |
| Camptothecin-11 | Targretin |
| Capecitabine | Taxol |

TABLE 1a-continued

| Chemotherapeutic Agents | |
|---|---|
| Carac | Taxotere |
| Carboplatin | Temodar |
| Carmustine | Temozolomide |
| Carmustine wafer | Teniposide |
| Casodex | TESPA |
| CCNU | Thalidomide |
| CDDP | Thalomid |
| CeeNU | TheraCys |
| Cerubidine | Thioguanine |
| cetuximab | Thioguanine Tabloid |
| Chlorambucil | Thiophosphoamide |
| Cisplatin | Thioplex |
| Citrovorum Factor | Thiotepa |
| Cladribine | TICE |
| Cortisone | Toposar |
| Cosmegen | Topotecan |
| CPT-11 | Toremifene |
| Cyclophosphamide | Trastuzumab |
| Cytadren | Tretinoin |
| Cytarabine | Trexall |
| Cytarabine liposomal | Trisenox |
| Cytosar-U | TSPA |
| Cytoxan | VCR |
| Dacarbazine | Velban |
| Dactinomycin | Velcade |
| Darbepoetin alfa | VePesid |
| Daunomycin | Vesanoid |
| Daunorubicin | Viadur |
| Daunorubicin hydrochloride | Vinblastine |
| Daunorubicin liposomal | Vinblastine Sulfate |
| DaunoXome | Vincasar Pfs |
| Decadron | Vincristine |
| Delta-Cortef | Vinorelbine |
| Deltasone | Vinorelbine tartrate |
| Denileukin diftitox | VLB |
| DepoCyt | VP-16 |
| Dexamethasone | Vumon |
| Dexamethasone acetate | Xeloda |
| dexamethasone sodium phosphate | Zanosar |
| Dexasone | Zevalin |
| Dexrazoxane | Zinecard |
| DHAD | Zoladex |
| DIC | Zoledronic acid |
| Diodex | Zometa |
| Docetaxel | Gliadel wafer |
| Doxil | Glivec |
| Doxorubicin | GM-CSF |
| Doxorubicin liposomal | Goserelin |
| Droxia | granulocyte-colony stimulating factor |
| DTIC | Granulocyte macrophage colony stimulating factor |
| DTIC-Dome | Halotestin |
| Duralone | Herceptin |
| Efudex | Hexadrol |
| Eligard | Hexalen |
| Ellence | Hexamethylmelamine |
| Eloxatin | HMM |
| Elspar | Hycamtin |
| Emcyt | Hydrea |
| Epirubicin | Hydrocort Acetate |
| Epoetin alfa | Hydrocortisone |
| Erbitux | Hydrocortisone sodium phosphate |
| Erwinia L-asparaginase | Hydrocortisone sodium succinate |
| Estramustine | Hydrocortone phosphate |
| Ethyol | Hydroxyurea |
| Etopophos | Ibritumomab |
| Etoposide | Ibritumomab Tiuxetan |
| Etoposide phosphate | Idamycin |
| Eulexin | Idarubicin |
| Evista | Ifex |
| Exemestane | IFN-alpha |
| Fareston | Ifosfamide |
| Faslodex | IL-2 |
| Femara | IL-11 |
| Filgrastim | Imatinib mesylate |
| Floxuridine | Imidazole Carboxamide |
| Fludara | Interferon alfa |

TABLE 1a-continued

Chemotherapeutic Agents

| | |
|---|---|
| Fludarabine | Interferon Alfa-2b (PEG conjugate) |
| Fluoroplex | Interleukin-2 |
| Fluorouracil | Interleukin-11 |
| Fluorouracil (cream) | Intron A (interferon alfa-2b) |
| Fluoxymesterone | Leucovorin |
| Flutamide | Leukeran |
| Folinic Acid | Leukine |
| FUDR | Leuprolide |
| Fulvestrant | Leurocristine |
| G-CSF | Leustatin |
| Gefitinib | Liposomal Ara-C |
| Gemcitabine | Liquid Pred |
| Gemtuzumab ozogamicin | Lomustine |
| Gemzar | L-PAM |
| Gleevec | L-Sarcolysin |
| Lupron | Meticorten |
| Lupron Depot | Mitomycin |
| Matulane | Mitomycin-C |
| Maxidex | Mitoxantrone |
| Mechlorethamine | M-Prednisol |
| Mechlorethamine Hydrochlorine | MTC |
| Medralone | MTX |
| Medrol | Mustargen |
| Megace | Mustine |
| Megestrol | Mutamycin |
| Megestrol Acetate | Myleran |
| Melphalan | Iressa |
| Mercaptopurine | Irinotecan |
| Mesna | Isotretinoin |
| Mesnex | Kidrolase |
| Methotrexate | Lanacort |
| Methotrexate Sodium | L-asparaginase |
| Methylprednisolone | LCR |
| Mylocel | |
| Letrozole | |

Assays Useful for the Peptides Disclosed Herein

Angiogenesis assays known in the art may be used. See, for example, U.S. Patent Application 2003/0077261A1 to Paris, et al. wherein rat aortic ring, bovine, mouse and human angiogenesis assays are described.

Quantification of ring microvessel outgrowths as described, for example, in U.S. Patent Application 2003/0077261A1 to Paris, et al. may be used wherein ring cultures are photographed using a digital video camera linked to an OLYMPUS BX60 microscope and the outgrowth area is selectively measured and detected with the Image Pro Plus software.

Endothelial Cell Migration Assays, described in U.S. Patent Application 2003/0077261A1 to Paris, et al. may be used, where migration of human brain adult endothelial cells is evaluated using a modified Boyden chamber assay (BD BioCoat MATRIGEL Invasion Chamber), as described (Soker et al. 1998; Nakamura et al. 1997).

Nude Mouse Tumor Xenograft models as described, for example, in U.S. Patent Application 2003/0077261A1 to Paris, et al. may be used wherein A-549 (human lung adenocarcinoma) and U87-MG (human glioblastoma) cells are implanted into 8-week-old female nude mice. Tumors grown in the animals are measuring before, after and during treatment with Aβ peptides. On the termination day of each in vivo antitumor study, tumors are extracted and microvessels are quantified.

The invention will be understood in further detail in view of the following nonlimiting examples.

EXAMPLES

Example 1

Cell Culture and Reagents

All in-vitro experiments were performed using primary Human Umbilical Vein Endothelial Cells (HUVEC) at passages 3-4, purchased from American Tissue Type Culture Collection (ATCC, VA). Cells were cultured in F12K Medium (ATCC, VA) supplemented with 10% fetal bovine serum (Invitrogen, CA), 0.1 mg/ml Heparin and 0.03 mg/ml endothelial cell growth supplement (Sigma-Aldrich, MO). At all times, cells were maintained in a sterile cell culture incubator at 37° C. and 5% $CO_2$.

Example 2

Preparation of Aβ Peptides

All peptides were prepared by and purchased from Biosource, CA upon request. 1 mg of lyophilized peptides were dissolved in 1 ml of 1,1,1,3,3,3-hexafluoro-2-propanol (HFIP) in order to minimize formation of β-sheet structures and promote α-helical secondary structure. Peptides were allowed to air dry in a chemical fume hood for one hour, followed by further drying in a speed-vac (Thermo-Savant, NY) for 30 minutes. The resulting clear film was re-suspended in 100% dimethylsulfoxide (DMSO) to a concentration of 1 mM. Peptides were subsequently aliquoted and stored at −80° C.

Example 3

Capillary Tube Formation Assay

HUVEC ($7.5 \times 10^4$ cells/ml) in 500 µl of medium were seeded in 24-well plates, on top of a layer of Matrigel basement membrane matrix (Invitrogen, CA) in F12K medium (ATCC, VA) containing 4% serum (Invitrogen, CA), 0.1 mg/ml Heparin and 0.03 mg/ml endothelial cell growth supplement (Sigma-Aldrich, MO). Cells were incubated with peptides (or control conditions) for 24 hours. Control wells received the same volume of vehicle (DMSO) used to dilute the peptides. Network formation experiments were performed in triplicate, and at least 2 randomly chosen fields were photographed for each well using a 4× objective. Capillary length was measured using Image Pro Plus software (Media Cybernetic, Inc., MD).

Example 4

Cell Proliferation Assay

HUVEC ($5 \times 10^3$ cells per well) were seeded in a 96 well plate. Cells were incubated with peptides (or control conditions) for 24 hours. A quick cell proliferation assay was performed as per the manufacturer's protocol (Biovision Inc., CA).

Example 5

Cell Adhesion Assay

HUVEC ($1 \times 10^4$ cells per well) were seeded in a 96 well plate pre-coated with basement membrane protein complex.

Cells were incubated with peptides (or control conditions) for 2.5 hours. For measurement of cell adhesion, the Innocyte cell adhesion assay was used (Calbiochem, CA) and the protocol followed as per the manufacturer's recommendations.

Example 6

Rat Corneal Micropocket Assay

This assay was carried out as described previously (Paris D, Townsend K, Quadros A, Humphrey J, Sun J, Brem S, Wotoczek-Obadia M, DelleDonne A, Patel N, Obregon D F, Crescentini R, Abdullah L, Coppola D, Rojiani A M, Crawford F, Sebti S M, Mullan M. (2004) Angiogenesis. 7, 75-85), using hydron pellets containing either VEGF (200 ng) alone, or in combination with different amounts of Aβ peptide fragments. The vascular growth response was measured seven days post implantation. The lengths and widths of vessel outgrowths were measured and the angiogenic index (AI) calculated using the formula L×W=AI. Rats were perfused with colloidal carbon, eyes enucleated and fixed in 10% buffered formalin. Corneas were removed under an Olympus dissecting microscope and mounted on glass slides with Crystal Mount media.

Example 7

Statistical Analysis

Statistical analyses were performed using ANOVA with post-hoc comparisons using Scheffe's or Bonferroni's using SPSS for Windows release 10.1.

Example 8

Effect of Aβ Peptide Fragments on Capillary Tube Formation

Various Aβ peptides and peptide fragments were tested for their ability to inhibit capillary network formation in the assay described in Example 3, including $A\beta_{1-42}$, $A\beta_{1-40}$, $A\beta_{1-28}$, $A\beta_{12-28}$, $A\beta_{17-28}$, $A\beta_{25-35}$, $A\beta_{10-35}$, $A\beta_{10-16}$ and $A\beta_{34-42}$) at 1, 5 and 10 µM. Total length of capillary tubes was quantified for each treatment group (n≧8), and expressed as a percentage of control treatment (FIG. 1).

Post hoc analysis revealed significant differences between control and $A\beta_{1-40}$, $A\beta_{1-42}$, $A\beta_{1-28}$, $A\beta_{10-35}$ and $A\beta_{12-28}$ at the 5 and 10 µM doses (P<0.005). Of the peptides tested, $A\beta_{1-28}$, $A\beta_{12-28}$, $A\beta_{10-35}$, $A\beta_{1-40}$ and $A\beta_{1-42}$ were the most active. $A\beta_{25-35}$ was slightly active at 5 µM, but not at 10 µM, and the other peptides ($A\beta_{10-16}$, $A\beta_{17-28}$ and $A\beta_{34-42}$) did not display any anti-angiogenic activity (FIG. 1). On the contrary, $A\beta_{34-42}$ promoted angiogenesis in a dose dependent manner. These data suggest that the minimal sequence required to preserve the anti-angiogenic activity of the Aβ peptide is included in residues 12-28. Furthermore, the observation that the $A\beta_{12-28}$ fragment is anti-angiogenic whereas the 17-28 fragment (missing the HHQK (SEQ ID NO:9) motif) is inactive suggests that the proteoglycan binding region (HHQK; (SEQ ID NO:9)) present between residues 13-16 is required for anti-angiogenic activity.

Example 9

Effect of Aβ Peptide Fragments on Cell Proliferation and Cell Adhesion

Various Aβ peptide fragments were tested for their ability to inhibit cellular proliferation and cellular adhesion to a basement membrane complex using the assays described in Example 4 and 5, respectively.

Figure 2A:
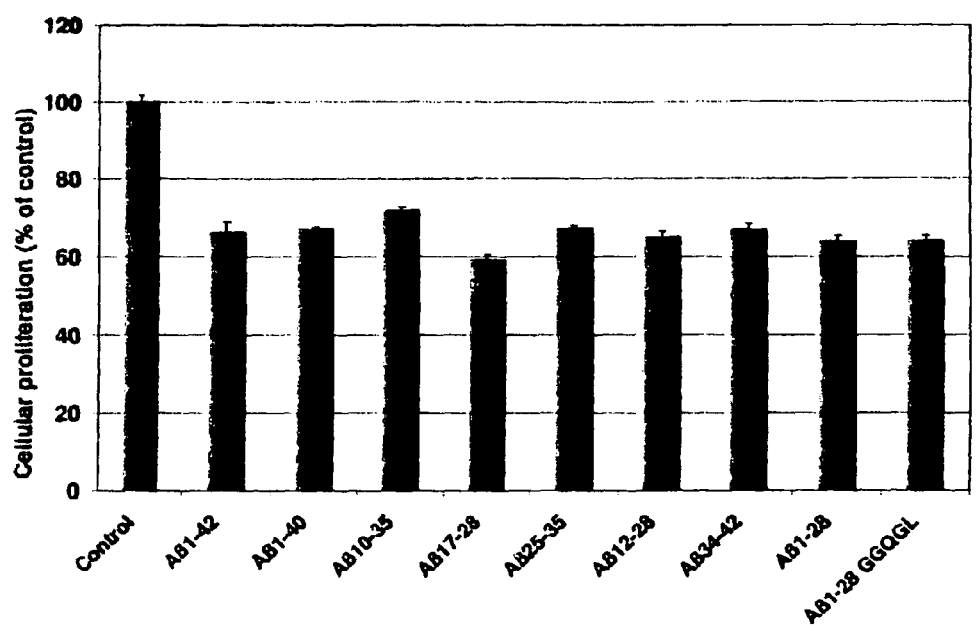
FIGS. 2A and 2B are charts of the cellular proliferation and cellular adhesion of HUVEC samples, expressed as a percentage of the control, after incubation with various Aβ peptide fragments as described in Example 9.
Figure 2B:
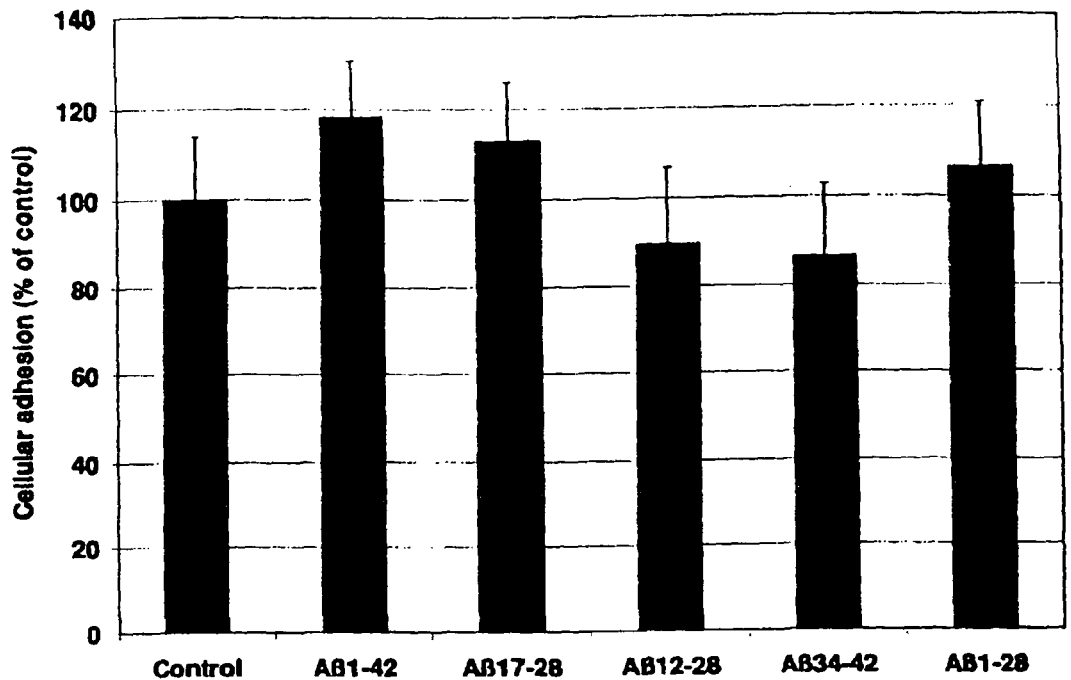

All peptide treatments significantly inhibited cellular proliferation (P<0.005). ANOVA revealed no significant main effects between any of the peptides tested. Post hoc testing revealed no significant differences between the different peptides (P>0.005). Whilst all the fragments tested were able to inhibit cell proliferation of HUVEC, there were no appreciable differences in potency between the different peptides (FIG. 2a). However, both ANOVA and post hoc testing revealed that none of the fragments tested were able to significantly affect cellular adhesion to a basement membrane complex comprising laminin, collagen IV, heparan sulfate proteoglycans and entactin (P>0.005) (FIG. 2b). The differences in anti-angiogenic activity of the Aβ peptide fragments could therefore not be related to effects on cellular proliferation or adhesion.

Example 10

Effect of Heparin on Capillary Tube Formation

In order to verify the importance of the putative heparin binding sequence within the Aβ peptide, heparin was added to the samples and the anti-angiogenic activity of Aβ peptide was quantified using the capillary tube formation assay described in Example 3.

Figure 3:
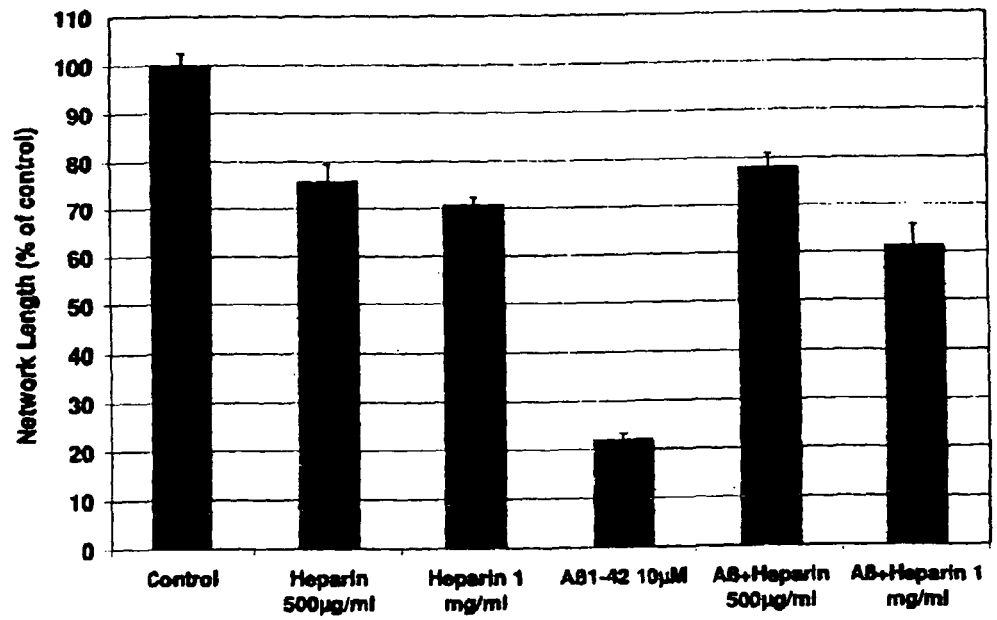
FIG. 3 is a chart of the total length of capillary tubes expressed as a percentage of control treatment versus treatment with heparin (0.5 or 1 mg/ml), $A\beta_{1-42}$ peptide, Aβ+heparin (500 μg/ml) and Aβ+heparin (1 mg/ml) as described in Example 10.

Total length of capillary tubes was quantified for each treatment group (n≧8), and expressed as a percentage of control treatment. Post hoc analysis revealed significant differences between control and all treatment groups (P<0.001), between Aβ and Aβ+heparin 500 µg/ml (P<0.001), Aβ and Aβ+heparin 1 mg/ml (P<0.001). The addition of 500 µg/ml and 1 mg/ml of heparin effectively reversed inhibition of capillary tube formation induced by $A\beta_{1-42}$ (FIG. 3). Addition of heparin alone also caused a slight inhibition of angiogenesis.

Example 11

Effect of Proteoglycan Binding Region Mutant Aβ Peptide Fragments on Capillary Tube Formation Since the addition of heparin reversed the anti-angiogenic activity of $A\beta_{1-42}$, it was hypothesized that the proteoglycan binding region within the peptide may be critical for imparting anti-angiogenic activity. To test this hypothesis, amino acid substitutions, that are known to effectively prevent the binding of Aβ to heparan sulfate proteoglycans (substitution of three amino acids present in the HHQK (SEQ ID NO:9) proteoglycan binding motif for either GGQG (SEQ ID NO:81), or AAQA SEQ ID NO:82)) (McLaurin et al. Eur. J. Biochem. 2000, 267, 6353-61; Olofssen, et al. J. Biol. Chem. 2005, October 7, advance electronic publication), were made to one of anti-angiogenic peptide fragments ($A\beta_{1-28}$). The effect of the mutant Aβ peptide fragments were then tested in the capillary tube formation assay described in Example 3.

Total length of capillary tubes was quantified for each treatment group (n≧8), and expressed as a percentage of control. ANOVA revealed significant dose dependent main effects of wildtype $A\beta_{1-28}$ (P<0.001), but no main effect of $A\beta_{1-28}$ GGQGL (P=0.566), or $A\beta_{1-28}$ AAQAL (P=0.380). Post hoc analysis revealed significant effects of wildtype $A\beta_{1-28}$ at 1, 5 and 10 µM (P<0.005), but no significant effects of the mutant $A\beta_{1-28}$ peptides at any of the doses tested.

Figure 4:
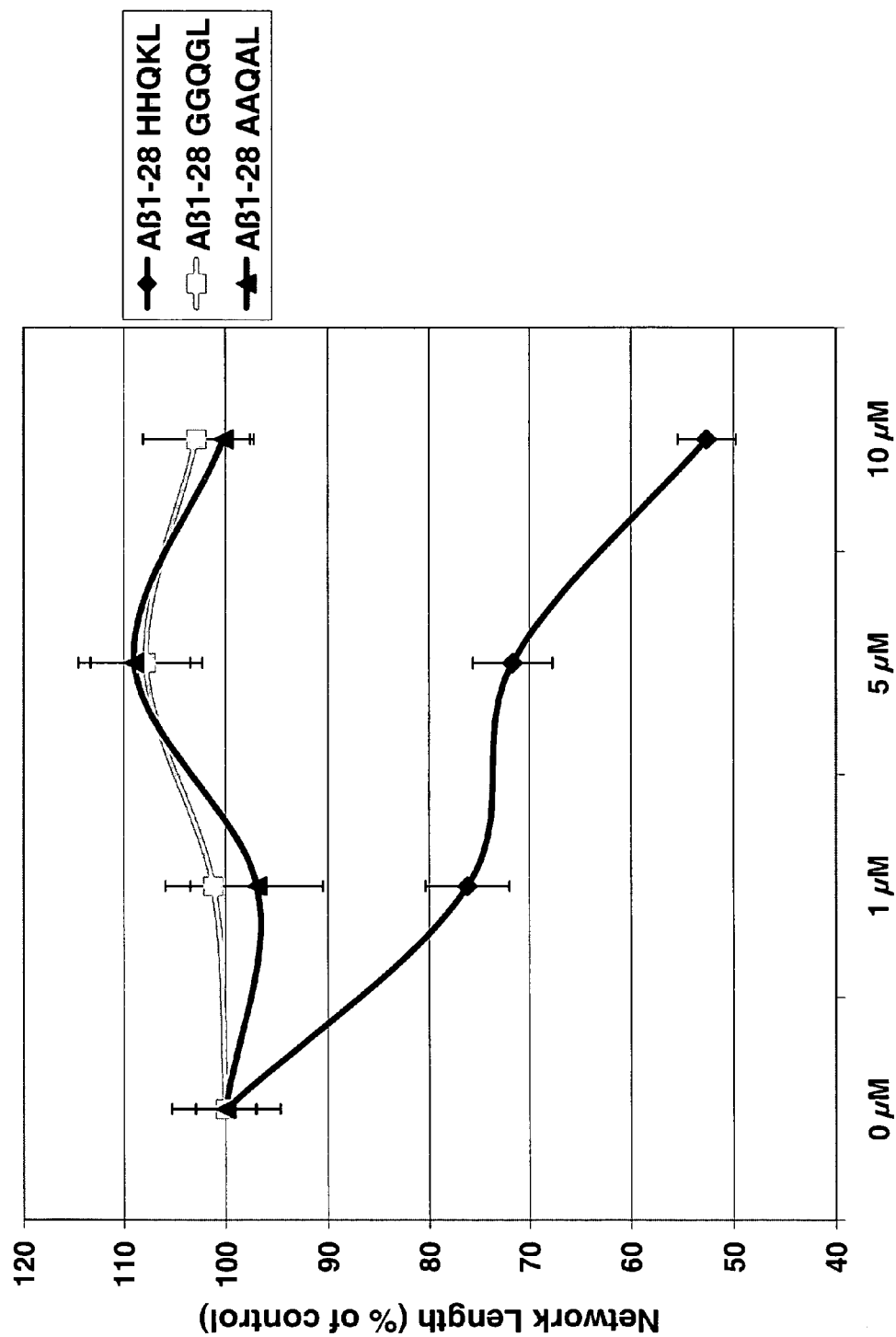
FIG. 4 is a graph of the total length of capillary tubes expressed as a percentage of control treatment for 0, 1, 5 and 10 μM doses of $A\beta_{1-28}$ (SEQ ID NO:2), $A\beta_{1-28}$ GGQGL (SEQ ID NO:3) and $A\beta_{1-28}$ AAQAL (SEQ ID NO:4) as described in Example 11.
Figure 5:
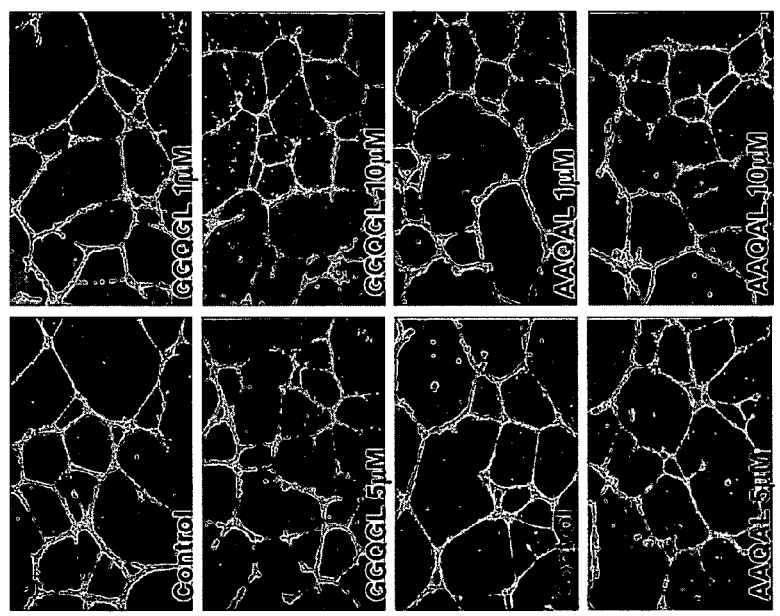
FIG. 5 provides photographs (at 4× magnification) of capillaries tubes formed following incubation with Aβ peptide fragments as described in Example 11.

Amino acid substitutions in the proteoglycan binding region of Aβ completely abolished the anti-angiogenic activity of the Aβ$_{1-28}$ peptide (FIG. 4) (see Table 2 for a list of peptide sequences).

TABLE 2

Summary of anti-angiogenic activity of Aβ peptide sequences at 10 μM

| Peptide | Amino Acid Sequence | Anti-angiogenic? | SEQ ID NO |
|---|---|---|---|
| Aβ$_{1-42}$ | DAEFRHDSGYEVHHQKLVFFAEDVGSNKGAII GLMVGGVVIA | Y | 83 |
| Aβ$_{1-40}$ | DAEFRHDSGYEVHHQKLVFFAEDVGSNKGAII GLMVGGVV | Y | 84 |
| Aβ$_{12-28}$ | VHHQKLVFFAEDVGSNK | Y | 8 |
| Aβ$_{17-28}$ | LVFFAEDVGSNK | N | 85 |
| Aβ$_{10-35}$ | YEVHHQKLVFFAEDVGSNKGAIIGLM | Y | 86 |
| Aβ$_{25-35}$ | GSNKGAIIGLM | N | 87 |
| Aβ$_{10-16}$ | YEVHHQK | N | 88 |
| Aβ$_{34-42}$ | LMVGGVVIA | N | 89 |
| Aβ$_{1-28}$ Wildtype | DAEFRHDSGYEVHHQKLVFFAEDVGSNK | Y | 2 |
| Aβ$_{1-28}$ Mutant 1 | DAEFRHDSGYEVGGQGLVFFAEDVGSNK | N | 3 |
| Aβ$_{1-28}$ Mutant 2 | DAEFRHDSGYEVAAQALVFFAEDVGSNK | N | 4 |
| Fragment 1 | HHHQKLVFF | Y | 5 |
| Fragment 2 | VHHQKLVII | N | 6 |
| Fragment 3 | VHHQKLVKK | N | 7 |

Example 12

Effect of LVFF Mutant Aβ Peptide Fragments on Capillary Tube Formation

The role of the VFF amino acid sequence adjacent on the C-terminal side of the HHQK (SEQ ID NO:9) sequence was established by testing peptide fragments consisting of 9 amino acids starting at the HHQK (SEQ ID NO:9) sequence (table 2, fragments 1-3) in the capillary tube formation assay described in Example 3.

Total length of capillary tubes was quantified for each treatment group (n≧6), and expressed as a percentage of control. ANOVA revealed significant main effect for the wildtype (HHHQKLVFF; (SEQ ID NO:5)), but not for the mutant peptides. Post hoc analysis revealed significant effects of wildtype peptide at 1, 5 and 10 μM (P<0.005), but no significant effects of the LVFF mutant peptides at any of the doses tested.

Figure 6:
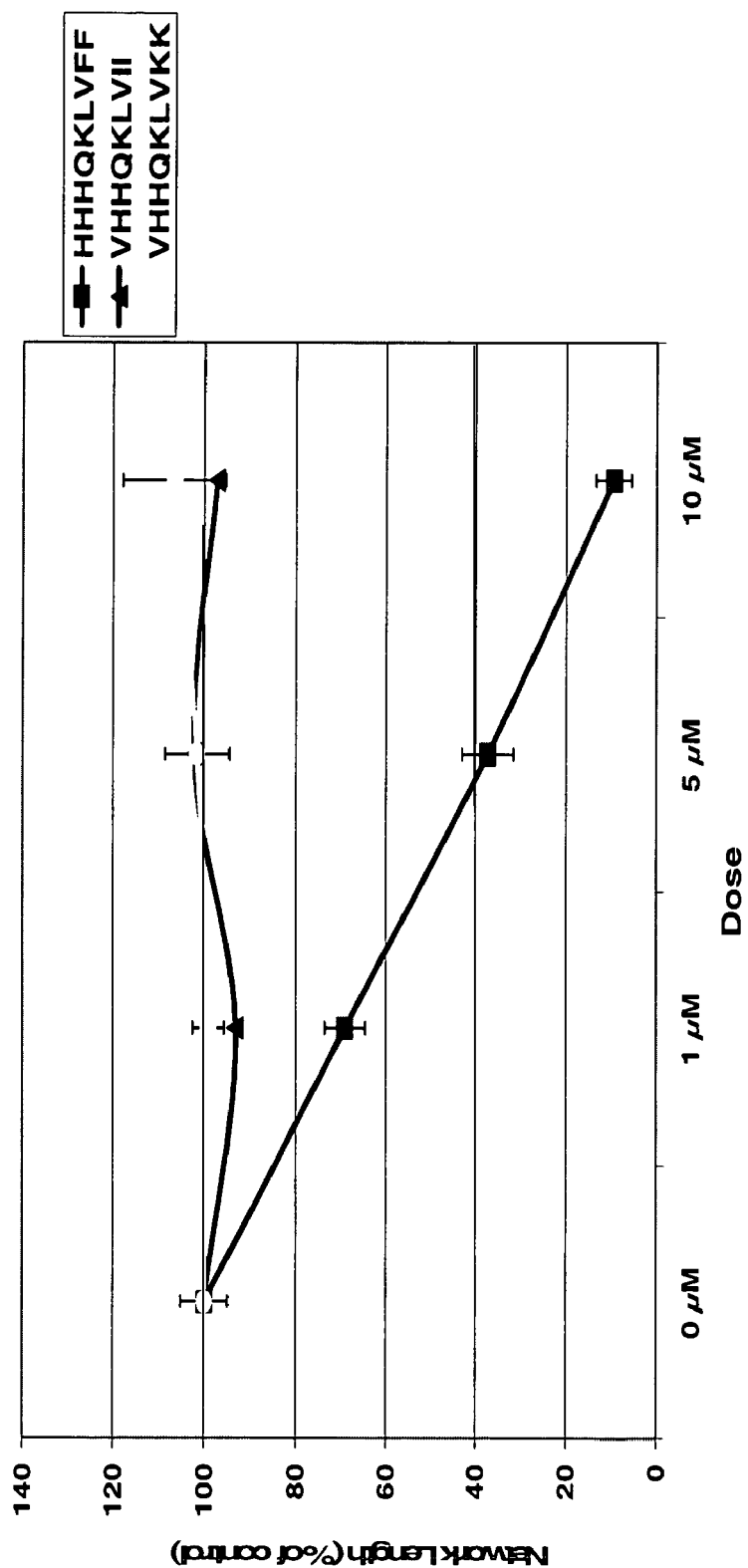
FIG. 6 is a graph of the total length of capillary tubes expressed as a percentage of control treatment for 0, 1, 5 and 10 μM doses of the peptides HHHQKLVFF (SEQ ID NO:5), VHHQKLVII (SEQ ID NO:6), and VHHQKLVKK (SEQ ID NO:7) as described in Example 12.

These results support that only a peptide sequence containing both the HHQK (SEQ ID NO:9) and the VFF motif effectively inhibits angiogenesis in capillary tube formation assay (FIG. 6). However, the Aβ$_{10-16}$ fragment containing only the YEVHHQK (SEQ ID NO:90) sequence is inactive, showing that this region alone is not sufficient for anti-angiogenic activity.

Example 13

Effect of Aβ$_{12-28}$ Peptide Fragments in the Rat Corneal Micropocket Assay

In order to determine whether Aβ$_{12-28}$ peptide fragment that appeared to be anti-angiogenic in-vitro was also anti-angiogenic in-vivo, Aβ$_{12-28}$ was tested in the rat corneal micropocket assay described in Example 6. Corneal micropockets were incubated for 7 days. Quantification of data from the rat corneal micropocket assay in response to 200 ng VEGF, VEGF+0.5 μg Aβ$_{12-28}$, VEGF+2.5 μg Aβ$_{12-28}$ and VEGF+5.0 μg Aβ$_{12-28}$. ANOVA revealed significant main effect of Aβ dose and post hoc analysis revealed a significant effect at the 5 μg dose (P<0.001). Angiogenesis indexes are represented as mean+/−SEM.

Figure 7:
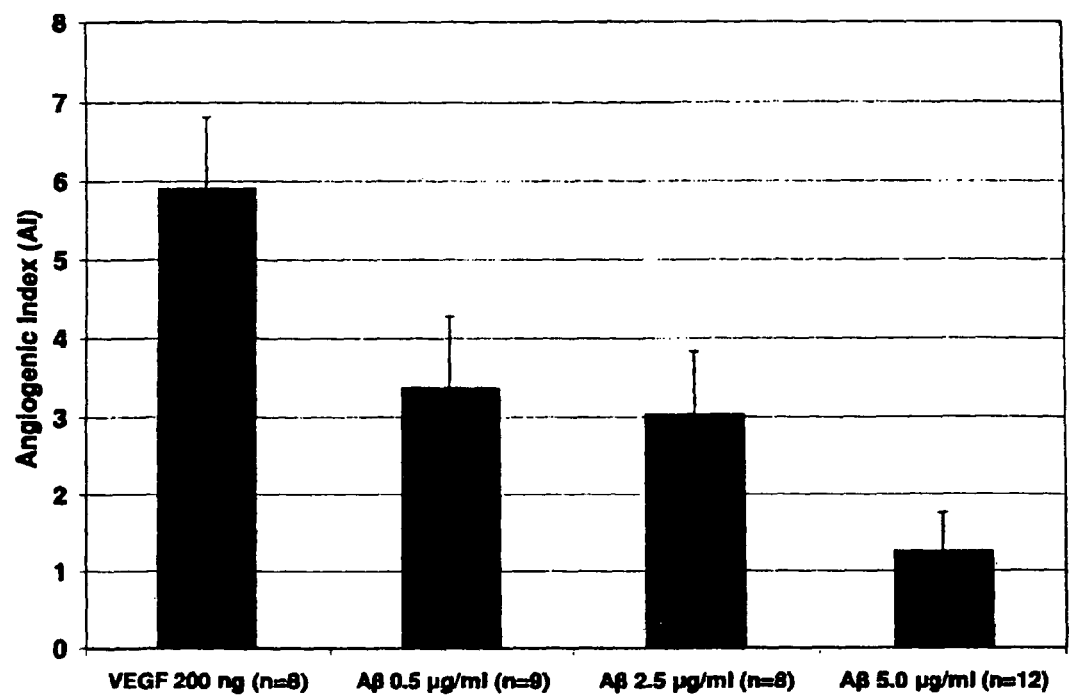
FIG. 7 is a chart of the Angiogenic Index (AI) for the rat corneal micropocket assay in response to 200 ng VEGF, VEGF+0.5 μg $A\beta_{12-28}$ (SEQ ID NO:8), VEGF+2.5 μg $A\beta_{12-28}$ (SEQ ID NO:8) and VEGF+5.0 μg $A\beta_{12-28}$ (SEQ ID NO:8) as described in Example 13.

These results support that Aβ$_{12-28}$ is able to dose dependently inhibit VEGF-induced angiogenesis in this in-vivo assay (FIG. 7), confirming data from in-vitro experiments.

Example 14

Figure 8:
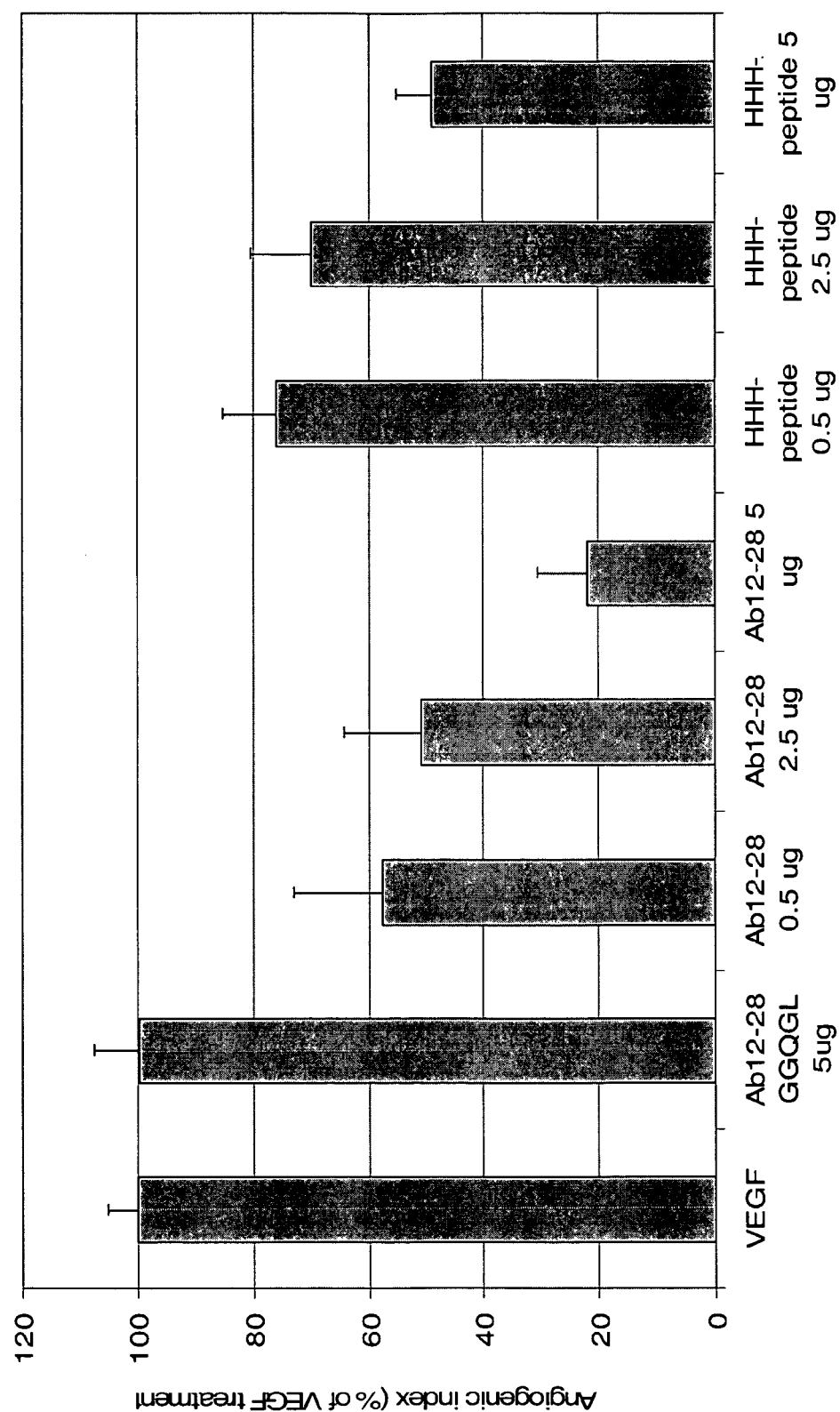
FIG. 8 is a chart of the Angiogenic Index (AI) for the rat corneal micropocket assay in response to VEGF, 5 ug $A\beta_{1-28}$ GGQGL (SEQ ID NO:3), and 0.5 ug, 2.5 ug and 5 ug of $A\beta_{12-28}$ (SEQ ID NO:8) and HHH-peptide (HHHQKLVFF; (SEQ ID NO:5)), as described in Example 14.
Figure 9:
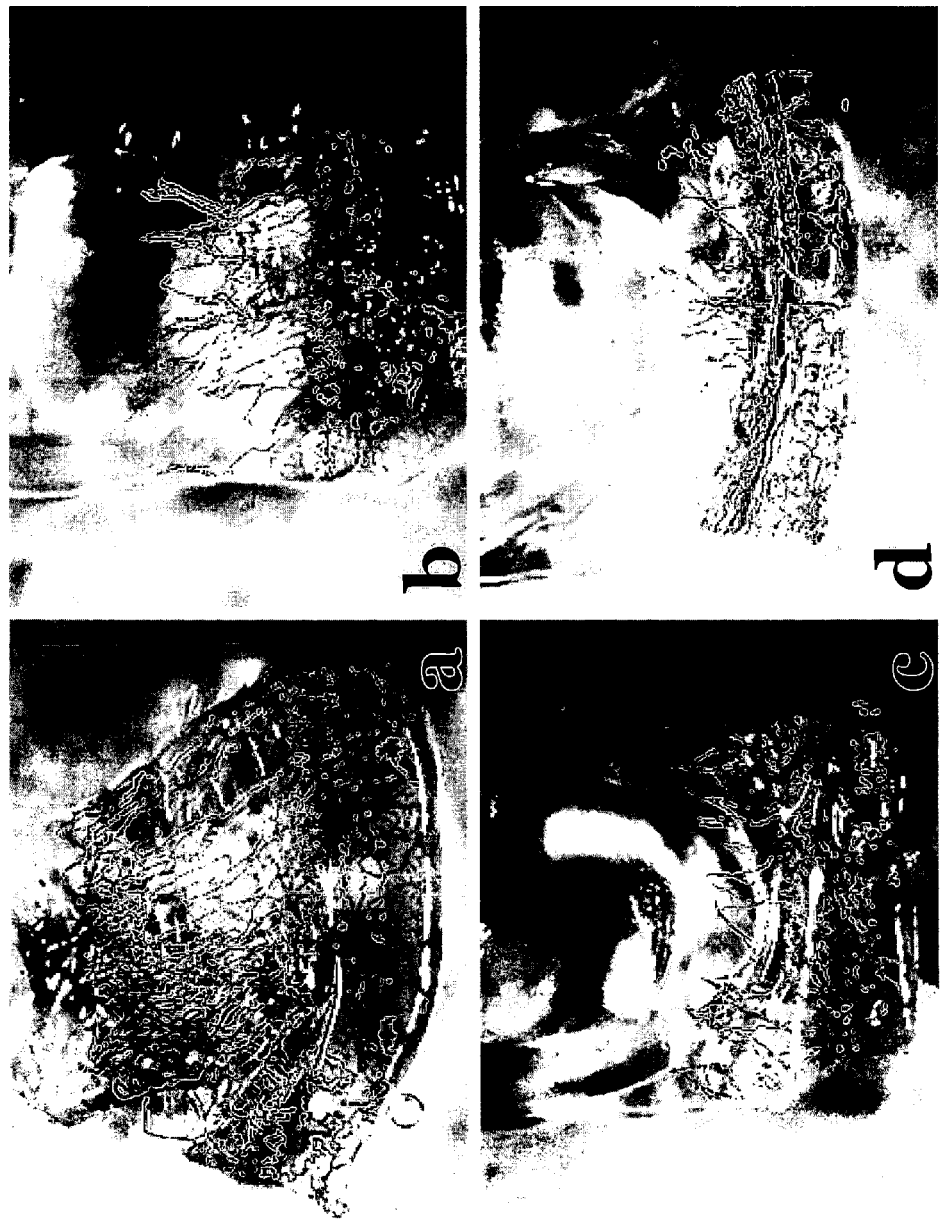
FIG. 9 provides representative photographs of rat corneal micropockets following a seven day incubation as described in Example 14, including a VEGF control and 0.5 μg, 2.5 μg and 5.0 μg of $A\beta_{12-28}$ (SEQ ID NO:8).

Effect of Aβ$_{12-28}$, Aβ$_{12-28}$ Mutants and Aβ$_{13-20}$ in the Rat Corneal Micropocket Assay Following the rat corneal micropocket assay method described in Example 6, the effect of various Aβ peptide fragments and mutants was tested. Quantification of data from the assay in response to response to 200 ng VEGF, 5.0 μg of the Aβ$_{12-28}$ GGQGL mutant peptide and 0.5 μg, 2.5 μg and 5.0 μg of Aβ$_{12-28}$ and Aβ$_{13-20}$ (HHH-peptide or HHQKLVFF (SEQ ID NO:1)). Aβ$_{12-28}$ GGQGL mutant is inactive at inhibiting angiogenesis in vivo. The shorter HHH-peptide appears antiangiogenic in vivo (P<0.05 in a dose dependent manner). Results are shown in FIG. 8. 4× magnified photographs of the capillaries are shown in FIG. 9.

SEQUENCE LISTING

<160> NUMBER OF SEQ ID NOS: 90

<210> SEQ ID NO 1
<211> LENGTH: 8
<212> TYPE: PRT
<213> ORGANISM: Homo sapiens

<400> SEQUENCE: 1

```
His His Gln Lys Leu Val Phe Phe
1               5

<210> SEQ ID NO 2
<211> LENGTH: 28
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys
            20                  25

<210> SEQ ID NO 3
<211> LENGTH: 28
<212> TYPE: PRT
<213> ORGANISM: Artificial Sequence
<220> FEATURE:
<223> OTHER INFORMATION: Homo sapiens

<400> SEQUENCE: 3

Asp Ala Glu Phe Arg His Asp Ser Gly Tyr Glu Val Gly Gly Gln Gly
1               5                   10                  15

Leu Val Phe Phe Ala Glu Asp Val Gly Ser Asn Lys
            20                  25

<210> SEQ ID NO 4
<211> LENGTH: 28
<212> TYPE: PRT
<213> ORGANISM: Artificial Sequence
<220> FEATURE:
<223> OTHER INFORMATION: Homo sapiens

<400> SEQUENCE: 4

Asp Ala Glu Phe Arg His Asp Ser Gly Tyr Glu Val Ala Ala Gln Ala
1               5                   10                  15

Leu Val Phe Phe Ala Glu Asp Val Gly Ser Asn Lys
            20                  25

<210> SEQ ID NO 5
<211> LENGTH: 9
<212> TYPE: PRT
<213> ORGANISM: Artificial Sequence
<220> FEATURE:
<223> OTHER INFORMATION: Homo sapiens

<400> SEQUENCE: 5

His His His Gln Lys Leu Val Phe Phe
1               5

<210> SEQ ID NO 6
<211> LENGTH: 9
<212> TYPE: PRT
<213> ORGANISM: Artificial Sequence
<220> FEATURE:
<223> OTHER INFORMATION: Homo sapiens

<400> SEQUENCE: 6

Val His His Gln Lys Leu Val Ile Ile
1               5

<210> SEQ ID NO 7
<211> LENGTH: 9
<212> TYPE: PRT
<213> ORGANISM: Artificial Sequence
```

```
<220> FEATURE:
<223> OTHER INFORMATION: Homo sapiens

<400> SEQUENCE: 7

Val His His Gln Lys Leu Val Lys Lys
1               5

<210> SEQ ID NO 8
<211> LENGTH: 17
<212> TYPE: PRT
<213> ORGANISM: Homo sapiens

<400> SEQUENCE: 8

Val His His Gln Lys Leu Val Phe Phe Ala Glu Asp Val Gly Ser Asn
1               5                   10                  15

Lys

<210> SEQ ID NO 9
<211> LENGTH: 4
<212> TYPE: PRT
<213> ORGANISM: Homo sapiens

<400> SEQUENCE: 9

His His Gln Lys
1

<210> SEQ ID NO 10
<211> LENGTH: 4
<212> TYPE: PRT
<213> ORGANISM: Homo sapiens

<400> SEQUENCE: 10

Leu Val Phe Phe
1

<210> SEQ ID NO 11
<211> LENGTH: 8
<212> TYPE: PRT
<213> ORGANISM: Artificial Sequence
<220> FEATURE:
<223> OTHER INFORMATION: Homo sapiens
<220> FEATURE:
<221> NAME/KEY: MISC_FEATURE
<222> LOCATION: (1)..(1)
<223> OTHER INFORMATION: Xaa at position 1 = Arg or His
<220> FEATURE:
<221> NAME/KEY: MISC_FEATURE
<222> LOCATION: (3)..(3)
<223> OTHER INFORMATION: Xaa at position 3 = Asn or Gln
<220> FEATURE:
<221> NAME/KEY: MISC_FEATURE
<222> LOCATION: (4)..(4)
<223> OTHER INFORMATION: Xaa at position 4 = Arg or Lys
<220> FEATURE:
<221> NAME/KEY: MISC_FEATURE
<222> LOCATION: (5)..(5)
<223> OTHER INFORMATION: Xaa at position 5 = Ile, Leu or Val
<220> FEATURE:
<221> NAME/KEY: MISC_FEATURE
<222> LOCATION: (6)..(6)
<223> OTHER INFORMATION: Xaa at position 6 = Ile, Leu or Val

<400> SEQUENCE: 11

Xaa His Xaa Xaa Xaa Xaa Phe Phe
1               5

<210> SEQ ID NO 12
<211> LENGTH: 8
<212> TYPE: PRT
```

```
<213> ORGANISM: Artificial Sequence
<220> FEATURE:
<223> OTHER INFORMATION: Homo sapiens

<400> SEQUENCE: 12

Arg His Gln Lys Leu Val Phe Phe
1               5

<210> SEQ ID NO 13
<211> LENGTH: 8
<212> TYPE: PRT
<213> ORGANISM: Artificial Sequence
<220> FEATURE:
<223> OTHER INFORMATION: Homo sapiens

<400> SEQUENCE: 13

His His Asn Lys Leu Val Phe Phe
1               5

<210> SEQ ID NO 14
<211> LENGTH: 8
<212> TYPE: PRT
<213> ORGANISM: Artificial Sequence
<220> FEATURE:
<223> OTHER INFORMATION: Homo sapiens

<400> SEQUENCE: 14

Arg His Asn Lys Leu Val Phe Phe
1               5

<210> SEQ ID NO 15
<211> LENGTH: 8
<212> TYPE: PRT
<213> ORGANISM: Artificial Sequence
<220> FEATURE:
<223> OTHER INFORMATION: Homo sapiens

<400> SEQUENCE: 15

His His Gln Arg Leu Val Phe Phe
1               5

<210> SEQ ID NO 16
<211> LENGTH: 8
<212> TYPE: PRT
<213> ORGANISM: Artificial Sequence
<220> FEATURE:
<223> OTHER INFORMATION: Homo sapiens

<400> SEQUENCE: 16

Arg His Gln Arg Leu Val Phe Phe
1               5

<210> SEQ ID NO 17
<211> LENGTH: 8
<212> TYPE: PRT
<213> ORGANISM: Artificial Sequence
<220> FEATURE:
<223> OTHER INFORMATION: Homo sapiens

<400> SEQUENCE: 17

His His Asn Arg Leu Val Phe Phe
1               5

<210> SEQ ID NO 18
<211> LENGTH: 8
<212> TYPE: PRT
<213> ORGANISM: Artificial Sequence
<220> FEATURE:
```

```
<223> OTHER INFORMATION: Homo sapiens

<400> SEQUENCE: 18

Arg His Asn Arg Leu Val Phe Phe
1               5

<210> SEQ ID NO 19
<211> LENGTH: 8
<212> TYPE: PRT
<213> ORGANISM: Artificial Sequence
<220> FEATURE:
<223> OTHER INFORMATION: Homo sapiens

<400> SEQUENCE: 19

His His Gln Lys Ile Val Phe Phe
1               5

<210> SEQ ID NO 20
<211> LENGTH: 8
<212> TYPE: PRT
<213> ORGANISM: Artificial Sequence
<220> FEATURE:
<223> OTHER INFORMATION: Homo sapiens

<400> SEQUENCE: 20

Arg His Gln Lys Ile Val Phe Phe
1               5

<210> SEQ ID NO 21
<211> LENGTH: 8
<212> TYPE: PRT
<213> ORGANISM: Artificial Sequence
<220> FEATURE:
<223> OTHER INFORMATION: Homo sapiens

<400> SEQUENCE: 21

His His Asn Lys Ile Val Phe Phe
1               5

<210> SEQ ID NO 22
<211> LENGTH: 8
<212> TYPE: PRT
<213> ORGANISM: Artificial Sequence
<220> FEATURE:
<223> OTHER INFORMATION: Homo sapiens

<400> SEQUENCE: 22

Arg His Asn Lys Ile Val Phe Phe
1               5

<210> SEQ ID NO 23
<211> LENGTH: 8
<212> TYPE: PRT
<213> ORGANISM: Artificial Sequence
<220> FEATURE:
<223> OTHER INFORMATION: Homo sapiens

<400> SEQUENCE: 23

His His Gln Arg Ile Val Phe Phe
1               5

<210> SEQ ID NO 24
<211> LENGTH: 8
<212> TYPE: PRT
<213> ORGANISM: Artificial Sequence
<220> FEATURE:
<223> OTHER INFORMATION: Homo sapiens
```

```
<400> SEQUENCE: 24

Arg His Gln Arg Ile Val Phe Phe
1               5

<210> SEQ ID NO 25
<211> LENGTH: 8
<212> TYPE: PRT
<213> ORGANISM: Artificial Sequence
<220> FEATURE:
<223> OTHER INFORMATION: Homo sapiens

<400> SEQUENCE: 25

His His Asn Arg Ile Val Phe Phe
1               5

<210> SEQ ID NO 26
<211> LENGTH: 8
<212> TYPE: PRT
<213> ORGANISM: Artificial Sequence
<220> FEATURE:
<223> OTHER INFORMATION: Homo sapiens

<400> SEQUENCE: 26

Arg His Asn Arg Ile Val Phe Phe
1               5

<210> SEQ ID NO 27
<211> LENGTH: 8
<212> TYPE: PRT
<213> ORGANISM: Artificial Sequence
<220> FEATURE:
<223> OTHER INFORMATION: Homo sapiens

<400> SEQUENCE: 27

His His Gln Lys Val Val Phe Phe
1               5

<210> SEQ ID NO 28
<211> LENGTH: 8
<212> TYPE: PRT
<213> ORGANISM: Artificial Sequence
<220> FEATURE:
<223> OTHER INFORMATION: Homo sapiens

<400> SEQUENCE: 28

Arg His Gln Lys Val Val Phe Phe
1               5

<210> SEQ ID NO 29
<211> LENGTH: 8
<212> TYPE: PRT
<213> ORGANISM: Artificial Sequence
<220> FEATURE:
<223> OTHER INFORMATION: Homo sapiens

<400> SEQUENCE: 29

His His Asn Lys Val Val Phe Phe
1               5

<210> SEQ ID NO 30
<211> LENGTH: 8
<212> TYPE: PRT
<213> ORGANISM: Artificial Sequence
<220> FEATURE:
<223> OTHER INFORMATION: Homo sapiens

<400> SEQUENCE: 30
```

```
Arg His Asn Lys Val Val Phe Phe
1               5

<210> SEQ ID NO 31
<211> LENGTH: 8
<212> TYPE: PRT
<213> ORGANISM: Artificial Sequence
<220> FEATURE:
<223> OTHER INFORMATION: Homo sapiens

<400> SEQUENCE: 31

His His Gln Arg Val Val Phe Phe
1               5

<210> SEQ ID NO 32
<211> LENGTH: 8
<212> TYPE: PRT
<213> ORGANISM: Artificial Sequence
<220> FEATURE:
<223> OTHER INFORMATION: Homo sapiens

<400> SEQUENCE: 32

Arg His Gln Arg Val Val Phe Phe
1               5

<210> SEQ ID NO 33
<211> LENGTH: 8
<212> TYPE: PRT
<213> ORGANISM: Artificial Sequence
<220> FEATURE:
<223> OTHER INFORMATION: Homo sapiens

<400> SEQUENCE: 33

His His Asn Arg Val Val Phe Phe
1               5

<210> SEQ ID NO 34
<211> LENGTH: 8
<212> TYPE: PRT
<213> ORGANISM: Artificial Sequence
<220> FEATURE:
<223> OTHER INFORMATION: Homo sapiens

<400> SEQUENCE: 34

Arg His Asn Arg Val Val Phe Phe
1               5

<210> SEQ ID NO 35
<211> LENGTH: 8
<212> TYPE: PRT
<213> ORGANISM: Artificial Sequence
<220> FEATURE:
<223> OTHER INFORMATION: Homo sapiens

<400> SEQUENCE: 35

His His Gln Lys Leu Ile Phe Phe
1               5

<210> SEQ ID NO 36
<211> LENGTH: 8
<212> TYPE: PRT
<213> ORGANISM: Artificial Sequence
<220> FEATURE:
<223> OTHER INFORMATION: Homo sapiens

<400> SEQUENCE: 36

Arg His Gln Lys Leu Ile Phe Phe
1               5
```

```
<210> SEQ ID NO 37
<211> LENGTH: 8
<212> TYPE: PRT
<213> ORGANISM: Artificial Sequence
<220> FEATURE:
<223> OTHER INFORMATION: Homo sapiens

<400> SEQUENCE: 37

His His Asn Lys Leu Ile Phe Phe
1               5

<210> SEQ ID NO 38
<211> LENGTH: 8
<212> TYPE: PRT
<213> ORGANISM: Artificial Sequence
<220> FEATURE:
<223> OTHER INFORMATION: Homo sapiens

<400> SEQUENCE: 38

Arg His Asn Lys Leu Ile Phe Phe
1               5

<210> SEQ ID NO 39
<211> LENGTH: 8
<212> TYPE: PRT
<213> ORGANISM: Artificial Sequence
<220> FEATURE:
<223> OTHER INFORMATION: Homo sapiens

<400> SEQUENCE: 39

His His Gln Arg Leu Ile Phe Phe
1               5

<210> SEQ ID NO 40
<211> LENGTH: 8
<212> TYPE: PRT
<213> ORGANISM: Artificial Sequence
<220> FEATURE:
<223> OTHER INFORMATION: Homo sapiens

<400> SEQUENCE: 40

Arg His Gln Arg Leu Ile Phe Phe
1               5

<210> SEQ ID NO 41
<211> LENGTH: 8
<212> TYPE: PRT
<213> ORGANISM: Artificial Sequence
<220> FEATURE:
<223> OTHER INFORMATION: Homo sapiens

<400> SEQUENCE: 41

His His Asn Arg Leu Ile Phe Phe
1               5

<210> SEQ ID NO 42
<211> LENGTH: 8
<212> TYPE: PRT
<213> ORGANISM: Artificial Sequence
<220> FEATURE:
<223> OTHER INFORMATION: Homo sapiens

<400> SEQUENCE: 42

Arg His Asn Arg Leu Ile Phe Phe
1               5
```

```
<210> SEQ ID NO 43
<211> LENGTH: 8
<212> TYPE: PRT
<213> ORGANISM: Artificial Sequence
<220> FEATURE:
<223> OTHER INFORMATION: Homo sapiens

<400> SEQUENCE: 43

His His Gln Lys Ile Ile Phe Phe
1               5

<210> SEQ ID NO 44
<211> LENGTH: 8
<212> TYPE: PRT
<213> ORGANISM: Artificial Sequence
<220> FEATURE:
<223> OTHER INFORMATION: Homo sapiens

<400> SEQUENCE: 44

Arg His Gln Lys Ile Ile Phe Phe
1               5

<210> SEQ ID NO 45
<211> LENGTH: 8
<212> TYPE: PRT
<213> ORGANISM: Artificial Sequence
<220> FEATURE:
<223> OTHER INFORMATION: Homo sapiens

<400> SEQUENCE: 45

His His Asn Lys Ile Ile Phe Phe
1               5

<210> SEQ ID NO 46
<211> LENGTH: 8
<212> TYPE: PRT
<213> ORGANISM: Artificial Sequence
<220> FEATURE:
<223> OTHER INFORMATION: Homo sapiens

<400> SEQUENCE: 46

Arg His Asn Lys Ile Ile Phe Phe
1               5

<210> SEQ ID NO 47
<211> LENGTH: 8
<212> TYPE: PRT
<213> ORGANISM: Artificial Sequence
<220> FEATURE:
<223> OTHER INFORMATION: Homo sapiens

<400> SEQUENCE: 47

His His Gln Arg Ile Ile Phe Phe
1               5

<210> SEQ ID NO 48
<211> LENGTH: 8
<212> TYPE: PRT
<213> ORGANISM: Artificial Sequence
<220> FEATURE:
<223> OTHER INFORMATION: Homo sapiens

<400> SEQUENCE: 48

Arg His Gln Arg Ile Ile Phe Phe
1               5

<210> SEQ ID NO 49
<211> LENGTH: 8
```

```
<212> TYPE: PRT
<213> ORGANISM: Artificial Sequence
<220> FEATURE:
<223> OTHER INFORMATION: Homo sapiens

<400> SEQUENCE: 49

His His Asn Arg Ile Ile Phe Phe
1               5

<210> SEQ ID NO 50
<211> LENGTH: 8
<212> TYPE: PRT
<213> ORGANISM: Artificial Sequence
<220> FEATURE:
<223> OTHER INFORMATION: Homo sapiens

<400> SEQUENCE: 50

Arg His Asn Arg Ile Ile Phe Phe
1               5

<210> SEQ ID NO 51
<211> LENGTH: 8
<212> TYPE: PRT
<213> ORGANISM: Artificial Sequence
<220> FEATURE:
<223> OTHER INFORMATION: Homo sapiens

<400> SEQUENCE: 51

His His Gln Lys Val Ile Phe Phe
1               5

<210> SEQ ID NO 52
<211> LENGTH: 8
<212> TYPE: PRT
<213> ORGANISM: Artificial Sequence
<220> FEATURE:
<223> OTHER INFORMATION: Homo sapiens

<400> SEQUENCE: 52

Arg His Gln Lys Val Ile Phe Phe
1               5

<210> SEQ ID NO 53
<211> LENGTH: 8
<212> TYPE: PRT
<213> ORGANISM: Artificial Sequence
<220> FEATURE:
<223> OTHER INFORMATION: Homo sapiens

<400> SEQUENCE: 53

His His Asn Lys Val Ile Phe Phe
1               5

<210> SEQ ID NO 54
<211> LENGTH: 8
<212> TYPE: PRT
<213> ORGANISM: Artificial Sequence
<220> FEATURE:
<223> OTHER INFORMATION: Homo sapiens

<400> SEQUENCE: 54

Arg His Asn Lys Val Ile Phe Phe
1               5

<210> SEQ ID NO 55
<211> LENGTH: 8
<212> TYPE: PRT
<213> ORGANISM: Artificial Sequence
```

<220> FEATURE:
<223> OTHER INFORMATION: Homo sapiens

<400> SEQUENCE: 55

His His Gln Arg Val Ile Phe Phe
1               5

<210> SEQ ID NO 56
<211> LENGTH: 8
<212> TYPE: PRT
<213> ORGANISM: Artificial Sequence
<220> FEATURE:
<223> OTHER INFORMATION: Homo sapiens

<400> SEQUENCE: 56

Arg His Gln Arg Val Ile Phe Phe
1               5

<210> SEQ ID NO 57
<211> LENGTH: 8
<212> TYPE: PRT
<213> ORGANISM: Artificial Sequence
<220> FEATURE:
<223> OTHER INFORMATION: Homo sapiens

<400> SEQUENCE: 57

His His Gln Lys Leu Leu Phe Phe
1               5

<210> SEQ ID NO 58
<211> LENGTH: 8
<212> TYPE: PRT
<213> ORGANISM: Artificial Sequence
<220> FEATURE:
<223> OTHER INFORMATION: Homo sapiens

<400> SEQUENCE: 58

Arg His Gln Lys Leu Leu Phe Phe
1               5

<210> SEQ ID NO 59
<211> LENGTH: 8
<212> TYPE: PRT
<213> ORGANISM: Artificial Sequence
<220> FEATURE:
<223> OTHER INFORMATION: Homo sapiens

<400> SEQUENCE: 59

His His Asn Lys Leu Leu Phe Phe
1               5

<210> SEQ ID NO 60
<211> LENGTH: 8
<212> TYPE: PRT
<213> ORGANISM: Artificial Sequence
<220> FEATURE:
<223> OTHER INFORMATION: Homo sapiens

<400> SEQUENCE: 60

Arg His Asn Lys Leu Leu Phe Phe
1               5

<210> SEQ ID NO 61
<211> LENGTH: 8
<212> TYPE: PRT
<213> ORGANISM: Artificial Sequence
<220> FEATURE:
<223> OTHER INFORMATION: Homo sapiens

```
<400> SEQUENCE: 61

His His Gln Arg Leu Leu Phe Phe
1               5

<210> SEQ ID NO 62
<211> LENGTH: 8
<212> TYPE: PRT
<213> ORGANISM: Artificial Sequence
<220> FEATURE:
<223> OTHER INFORMATION: Homo sapiens

<400> SEQUENCE: 62

Arg His Gln Arg Leu Leu Phe Phe
1               5

<210> SEQ ID NO 63
<211> LENGTH: 8
<212> TYPE: PRT
<213> ORGANISM: Artificial Sequence
<220> FEATURE:
<223> OTHER INFORMATION: Homo sapiens

<400> SEQUENCE: 63

His His Asn Arg Leu Leu Phe Phe
1               5

<210> SEQ ID NO 64
<211> LENGTH: 8
<212> TYPE: PRT
<213> ORGANISM: Artificial Sequence
<220> FEATURE:
<223> OTHER INFORMATION: Homo sapiens

<400> SEQUENCE: 64

Arg His Asn Arg Leu Leu Phe Phe
1               5

<210> SEQ ID NO 65
<211> LENGTH: 8
<212> TYPE: PRT
<213> ORGANISM: Artificial Sequence
<220> FEATURE:
<223> OTHER INFORMATION: Homo sapiens

<400> SEQUENCE: 65

His His Gln Lys Ile Leu Phe Phe
1               5

<210> SEQ ID NO 66
<211> LENGTH: 8
<212> TYPE: PRT
<213> ORGANISM: Artificial Sequence
<220> FEATURE:
<223> OTHER INFORMATION: Homo sapiens

<400> SEQUENCE: 66

Arg His Gln Lys Ile Leu Phe Phe
1               5

<210> SEQ ID NO 67
<211> LENGTH: 8
<212> TYPE: PRT
<213> ORGANISM: Artificial Sequence
<220> FEATURE:
<223> OTHER INFORMATION: Homo sapiens

<400> SEQUENCE: 67
```

```
His His Asn Lys Ile Leu Phe Phe
1               5

<210> SEQ ID NO 68
<211> LENGTH: 8
<212> TYPE: PRT
<213> ORGANISM: Artificial Sequence
<220> FEATURE:
<223> OTHER INFORMATION: Homo sapiens

<400> SEQUENCE: 68

Arg His Asn Lys Ile Leu Phe Phe
1               5

<210> SEQ ID NO 69
<211> LENGTH: 8
<212> TYPE: PRT
<213> ORGANISM: Artificial Sequence
<220> FEATURE:
<223> OTHER INFORMATION: Homo sapiens

<400> SEQUENCE: 69

His His Gln Arg Ile Leu Phe Phe
1               5

<210> SEQ ID NO 70
<211> LENGTH: 8
<212> TYPE: PRT
<213> ORGANISM: Artificial Sequence
<220> FEATURE:
<223> OTHER INFORMATION: Homo sapiens

<400> SEQUENCE: 70

Arg His Gln Arg Ile Leu Phe Phe
1               5

<210> SEQ ID NO 71
<211> LENGTH: 8
<212> TYPE: PRT
<213> ORGANISM: Artificial Sequence
<220> FEATURE:
<223> OTHER INFORMATION: Homo sapiens

<400> SEQUENCE: 71

His His Asn Arg Ile Leu Phe Phe
1               5

<210> SEQ ID NO 72
<211> LENGTH: 8
<212> TYPE: PRT
<213> ORGANISM: Artificial Sequence
<220> FEATURE:
<223> OTHER INFORMATION: Homo sapiens

<400> SEQUENCE: 72

Arg His Asn Arg Ile Leu Phe Phe
1               5

<210> SEQ ID NO 73
<211> LENGTH: 8
<212> TYPE: PRT
<213> ORGANISM: Artificial Sequence
<220> FEATURE:
<223> OTHER INFORMATION: Homo sapiens

<400> SEQUENCE: 73

His His Gln Lys Val Leu Phe Phe
```

-continued

```
<210> SEQ ID NO 74
<211> LENGTH: 8
<212> TYPE: PRT
<213> ORGANISM: Artificial Sequence
<220> FEATURE:
<223> OTHER INFORMATION: Homo sapiens

<400> SEQUENCE: 74

Arg His Gln Lys Val Leu Phe Phe
1               5

<210> SEQ ID NO 75
<211> LENGTH: 8
<212> TYPE: PRT
<213> ORGANISM: Artificial Sequence
<220> FEATURE:
<223> OTHER INFORMATION: Homo sapiens

<400> SEQUENCE: 75

His His Asn Lys Val Leu Phe Phe
1               5

<210> SEQ ID NO 76
<211> LENGTH: 8
<212> TYPE: PRT
<213> ORGANISM: Artificial Sequence
<220> FEATURE:
<223> OTHER INFORMATION: Homo sapiens

<400> SEQUENCE: 76

Arg His Asn Lys Val Leu Phe Phe
1               5

<210> SEQ ID NO 77
<211> LENGTH: 8
<212> TYPE: PRT
<213> ORGANISM: Artificial Sequence
<220> FEATURE:
<223> OTHER INFORMATION: Homo sapiens

<400> SEQUENCE: 77

His His Gln Arg Val Leu Phe Phe
1               5

<210> SEQ ID NO 78
<211> LENGTH: 8
<212> TYPE: PRT
<213> ORGANISM: Artificial Sequence
<220> FEATURE:
<223> OTHER INFORMATION: Homo sapiens

<400> SEQUENCE: 78

Arg His Gln Arg Val Leu Phe Phe
1               5

<210> SEQ ID NO 79
<211> LENGTH: 8
<212> TYPE: PRT
<213> ORGANISM: Artificial Sequence
<220> FEATURE:
<223> OTHER INFORMATION: Homo sapiens

<400> SEQUENCE: 79

His His Asn Arg Val Ile Phe Phe
1               5
```

```
<210> SEQ ID NO 80
<211> LENGTH: 8
<212> TYPE: PRT
<213> ORGANISM: Artificial Sequence
<220> FEATURE:
<223> OTHER INFORMATION: Homo sapiens

<400> SEQUENCE: 80

Arg His Asn Arg Val Ile Phe Phe
1               5

<210> SEQ ID NO 81
<211> LENGTH: 4
<212> TYPE: PRT
<213> ORGANISM: Artificial Sequence
<220> FEATURE:
<223> OTHER INFORMATION: Synthetic

<400> SEQUENCE: 81

Gly Gly Gln Gly
1

<210> SEQ ID NO 82
<211> LENGTH: 4
<212> TYPE: PRT
<213> ORGANISM: Artificial Sequence
<220> FEATURE:
<223> OTHER INFORMATION: Synthetic

<400> SEQUENCE: 82

Ala Ala Gln Ala
1

<210> SEQ ID NO 83
<211> LENGTH: 42
<212> TYPE: PRT
<213> ORGANISM: Homo sapiens

<400> SEQUENCE: 83

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 84
<211> LENGTH: 40
<212> TYPE: PRT
<213> ORGANISM: Homo sapiens

<400> SEQUENCE: 84

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 85
<211> LENGTH: 12
<212> TYPE: PRT
<213> ORGANISM: Homo sapiens

<400> SEQUENCE: 85
```

```
Leu Val Phe Phe Ala Glu Asp Val Gly Ser Asn Lys
1               5                   10
```

<210> SEQ ID NO 86
<211> LENGTH: 26
<212> TYPE: PRT
<213> ORGANISM: Homo sapiens

<400> SEQUENCE: 86

```
Tyr Glu Val His His Gln Lys Leu Val Phe Phe Ala Glu Asp Val Gly
1               5                   10                  15
Ser Asn Lys Gly Ala Ile Ile Gly Leu Met
            20                  25
```

<210> SEQ ID NO 87
<211> LENGTH: 11
<212> TYPE: PRT
<213> ORGANISM: Homo sapiens

<400> SEQUENCE: 87

```
Gly Ser Asn Lys Gly Ala Ile Ile Gly Leu Met
1               5                   10
```

<210> SEQ ID NO 88
<211> LENGTH: 7
<212> TYPE: PRT
<213> ORGANISM: Homo sapiens

<400> SEQUENCE: 88

```
Tyr Glu Val His His Gln Lys
1               5
```

<210> SEQ ID NO 89
<211> LENGTH: 9
<212> TYPE: PRT
<213> ORGANISM: Homo sapiens

<400> SEQUENCE: 89

```
Leu Met Val Gly Gly Val Val Ile Ala
1               5
```

<210> SEQ ID NO 90
<211> LENGTH: 7
<212> TYPE: PRT
<213> ORGANISM: Homo sapiens

<400> SEQUENCE: 90

```
Tyr Glu Val His His Gln Lys
1               5
```

The invention claimed is:

1. A method of treating a disease or disorder mediated by pathological angiogenesis comprising administering to a subject in need thereof a biologically active Aβ peptide, wherein the fragment is Aβ$_{10-35}$ (SEQ ID NO:86), Aβ$_{12-28}$ (SEQ ID NO:8) or Aβ$_{13-20}$ (SEQ ID NO:1) and the fragment is optionally in the form of a fusion protein comprising a heterologous protein sequence.

2. The method of claim 1, wherein the fragment is Aβ$_{10-35}$ (SEQ ID NO:86).

3. The method of claim 1, wherein the fragment is Aβ$_{12-28}$ (SEQ ID NO:8).

4. The method of claim 1, wherein the fragment is Aβ$_{13-20}$ (SEQ ID NO:1).

5. The method of claim 1, wherein the subject is a mammal.

6. The method of claim 1, wherein the subject is a human.

7. The method of claim 1, wherein the biologically active Aβ peptide fragment is administered by a route selected from the group consisting of oral, parenteral, intravenous, intraarterially, pulmonary, mucosal, topical, transdermal, subcutaneous, intramuscular, rectal, intracranial, intracerebroventricular, intracerebral, intravaginal, intrauterine, intrathecal or intraperitoneal administration.

8. The method of claim 1, wherein the biologically active Aβ peptide fragment is administered to the subject with a carrier.

9. The method of claim 1, wherein the Aβ peptide fragment is administered to the subject in a controlled release formulation.

10. The method of claim 1, wherein the controlled release formulation comprises a polymer matrix.

11. The method of claim 1, further comprising administering one more additional therapeutic agents in combination or alternation with the biologically active Aβ peptide fragment.

12. The method of claim 11, wherein the additional therapeutic agent is a chemotherapeutic agent.

13. The method according to claim 1, wherein the Aβ peptide fragment is administered to the patient as a fusion protein.

14. A method of treating a cancer mediated by pathological angiogenesis comprising administering to a subject in need thereof a biologically active Aβ peptide fragment selected from the group consisting of $A\beta_{10\text{-}35}$ (SEQ ID NO:86), $A\beta_{12\text{-}28}$ (SEQ ID NO:8) and $A\beta_{13\text{-}20}$ (SEQ ID NO:1).

15. The method of claim 14, wherein the fragment is $A\beta_{13\text{-}20}$ (SEQ ID NO:1).

16. The method of claim 14, wherein the subject is a mammal.

17. The method of claim 14, wherein the subject is a human.

18. The method of claim 14, further comprising administering one or more additional therapeutic agents.

19. The method of claim 18, wherein the additional therapeutic agent is a chemotherapeutic agent.

20. The method of claim 19, wherein the chemotherapeutic agent is selected from the group consisting of alkylating agents, nitrosoureas, antimetabolites, topoisomerase inhibitors, mitotic inhibitors, and corticosteroid inhibitors.

* * * * *